US011503984B2

(12) United States Patent
Surti et al.

(10) Patent No.: US 11,503,984 B2
(45) Date of Patent: Nov. 22, 2022

(54) DEFLECTING ENDOSCOPE ACCESSORY CHANNELS

(71) Applicant: Cook Medical Technologies LLC, Bloomington, IN (US)

(72) Inventors: Vihar C. Surti, Winston-Salem, NC (US); John C. Sigmon, Winston-Salem, NC (US); Smitha Smith, Winston-Salem, NC (US); Laura Johnson, Winston-Salem, NC (US); Andrea C. Mydosh, Winston-Salem, NC (US); Tyler E. McLawhorn, Winston-Salem, NC (US); Michael J. Brecht, Salisbury, NC (US); Gregory Hardy, Winston-Salem, NC (US); Shaun D. Gittard, Winston-Salem, NC (US); William S. Gibbons, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 554 days.

(21) Appl. No.: 15/445,518

(22) Filed: Feb. 28, 2017

(65) Prior Publication Data

US 2017/0251908 A1 Sep. 7, 2017

Related U.S. Application Data

(60) Provisional application No. 62/382,552, filed on Sep. 1, 2016, provisional application No. 62/301,705, filed on Mar. 1, 2016.

(51) Int. Cl.
*A61B 1/00* (2006.01)
*A61B 1/018* (2006.01)
(Continued)

(52) U.S. Cl.
CPC .......... *A61B 1/00098* (2013.01); *A61B 1/008* (2013.01); *A61B 1/0055* (2013.01);
(Continued)

(58) Field of Classification Search
CPC ............ A61B 1/00098; A61B 1/00174; A61B 1/0055; A61B 1/00114; A61B 1/00128;
(Continued)

(56) References Cited

U.S. PATENT DOCUMENTS 3,557,780 A   1/1971 Sato
3,896,793 A * 7/1975 Mitsui ................ A61B 1/00098
                                                        385/118
(Continued)

FOREIGN PATENT DOCUMENTS

CN   105078398 A   11/2015
EP   2 596 741 A1   5/2013
(Continued)

OTHER PUBLICATIONS

PCT Notice of Transmittal of International Search Report in related application No. PCT/US2017/019850 (5 pgs).
(Continued)

*Primary Examiner* — Timothy J Neal
(74) *Attorney, Agent, or Firm* — Crowell & Moring LLP

(57) ABSTRACT

A scope system is provided including an elongate tube with a distal portion and a lumen extending therethrough. The scope system also includes at least one accessory channel extending from a proximal end to a distal end and having with an accessory lumen extending therethrough, the at least one accessory channel movably disposed at least partially within the lumen of the elongate tube. The at least one accessory channel includes a distal section and a forward-viewing configuration and a side-viewing configuration. In the forward-viewing configuration, the distal section of the
(Continued)

at least one accessory channel is substantially parallel to the distal portion of the elongate tube and in the side-viewing configuration, the distal section of the at least one accessory channel is arced at a radius greater than a radius of the distal portion of the elongate tube.

21 Claims, 27 Drawing Sheets

(51) Int. Cl.
| | |
|---|---|
| A61B 1/005 | (2006.01) |
| A61B 1/008 | (2006.01) |
| A61B 1/05 | (2006.01) |
| A61B 1/06 | (2006.01) |
| A61B 1/273 | (2006.01) |

(52) U.S. Cl.
CPC ...... *A61B 1/00114* (2013.01); *A61B 1/00128* (2013.01); *A61B 1/00133* (2013.01); *A61B 1/00137* (2013.01); *A61B 1/00174* (2013.01); *A61B 1/018* (2013.01); *A61B 1/05* (2013.01); *A61B 1/0623* (2013.01); *A61B 1/0684* (2013.01); *A61B 1/273* (2013.01)

(58) Field of Classification Search
CPC . A61B 1/00133; A61B 1/00137; A61B 1/008; A61B 1/05; A61B 1/0623; A61B 1/0684; A61B 1/018; A61B 1/273; A61B 1/000133
See application file for complete search history.

(56) References Cited

U.S. PATENT DOCUMENTS

| | | | |
|---|---|---|---|
| 4,763,662 | A | 8/1988 | Yokoi |
| 5,005,558 | A | 4/1991 | Aomori |
| 5,143,475 | A | 9/1992 | Chikama |
| 5,749,828 | A | 5/1998 | Solomon et al. |
| 5,873,817 | A | 2/1999 | Kokish et al. |
| 6,071,279 | A | 6/2000 | Whayne et al. |
| 6,817,974 | B2 | 11/2004 | Cooper et al. |
| 8,771,171 | B2* | 7/2014 | Onuki ................. A61B 1/0052 600/104 |
| 9,408,529 | B2 | 8/2016 | Smith et al. |
| 9,565,994 | B2 | 2/2017 | Kappel et al. |
| 9,986,996 | B2 | 6/2018 | Hiernaux et al. |
| 10,029,073 | B2 | 7/2018 | Kabe et al. |
| 10,076,236 | B2 | 9/2018 | Ikeda et al. |
| 10,321,804 | B2 | 6/2019 | Jacobsen et al. |
| 10,363,398 | B2 | 7/2019 | Gerrans et al. |
| 2004/0138529 | A1 | 7/2004 | Wiltshire et al. |
| 2004/0249367 | A1* | 12/2004 | Saadat ................ A61B 1/0055 606/1 |
| 2005/0234297 | A1* | 10/2005 | Devierre ........... A61B 1/00087 600/153 |
| 2006/0178560 | A1 | 8/2006 | Saadat et al. |
| 2006/0189845 | A1* | 8/2006 | Maahs .................. A61B 1/018 600/146 |
| 2008/0097293 | A1 | 4/2008 | Chin |
| 2008/0287961 | A1* | 11/2008 | Miyamoto .......... A61B 1/0684 606/127 |
| 2008/0300462 | A1 | 12/2008 | Intoccia et al. |
| 2009/0171159 | A1 | 7/2009 | Jorgensen |
| 2010/0036198 | A1 | 2/2010 | Tacchino et al. |
| 2012/0041264 | A1* | 2/2012 | Blase ................ A61B 1/00078 600/121 |
| 2012/0170970 | A1 | 7/2012 | Kitagawa et al. |
| 2012/0238805 | A1 | 9/2012 | Iwasaka |
| 2013/0184528 | A1* | 7/2013 | Onuki ................ A61B 1/00135 600/146 |
| 2013/0231534 | A1* | 9/2013 | Piskun ................ A61B 1/0051 600/114 |
| 2014/0142393 | A1* | 5/2014 | Piskun ............... A61B 17/0206 600/206 |
| 2015/0032117 | A1 | 1/2015 | Kim et al. |
| 2015/0101442 | A1 | 4/2015 | Romo |
| 2016/0235400 | A1* | 8/2016 | Hiernaux ........... A61B 17/0469 |
| 2016/0288337 | A1 | 10/2016 | Zubiate et al. |
| 2017/0095645 | A1 | 4/2017 | Toth |
| 2017/0354318 | A1 | 12/2017 | Rogers et al. |
| 2018/0168432 | A1 | 6/2018 | Banik et al. |
| 2018/0360435 | A1 | 12/2018 | Romo |
| 2019/0104932 | A1 | 4/2019 | Ostrovsky et al. |
| 2019/0142413 | A1 | 5/2019 | Fairneny |

FOREIGN PATENT DOCUMENTS

| | | |
|---|---|---|
| GB | 2478988 | 9/2011 |
| JP | S61-280849 A | 12/1986 |
| JP | S62-74348 A | 4/1987 |
| JP | S62-292135 A | 12/1987 |
| JP | S63-155116 A | 6/1988 |
| JP | H01-138522 A | 5/1989 |
| JP | H10-295635 A | 11/1998 |
| JP | 2003-204926 A | 7/2003 |
| JP | 2005-152452 A | 6/2005 |
| JP | 2007-532262 A | 11/2007 |
| JP | 2008-536552 A | 9/2008 |
| JP | 2009-018044 A | 1/2009 |
| JP | 2009-529390 A | 8/2009 |
| JP | 2010-063772 A | 3/2010 |
| JP | 2010-284503 A | 12/2010 |
| JP | 2011-062362 A | 3/2011 |
| JP | 2011-072413 A | 4/2011 |
| JP | 2013-066638 A | 4/2013 |
| JP | 2014-102390 A | 6/2014 |
| JP | 2015-512661 A | 4/2015 |
| JP | 2016-513500 A | 5/2016 |
| KR | 10-2012-0111603 | 10/2012 |
| WO | WO 2007/063904 A1 | 5/2009 |
| WO | WO 2012/111761 | 8/2012 |

OTHER PUBLICATIONS

PCT Written Opinion of the International Searching Authority Report in related application No. PCT/US2017/019850 (8 pgs).
First Office Action from corresponding Korean Application No. 10-2018-7027795, dated Apr. 2, 2020, 7 pages, in Korean language.
First Office Action from corresponding Korean Application No. 10-2018-7027795, dated Apr. 2, 2020, 6 pages, English translation.
Second Office Action from corresponding Japanese Application No. JP 2018-545842, dated Mar. 3, 2020, 4 pages, in Japanese language.
Second Office Action from corresponding Japanese Application No. JP 2018-545842, dated Mar. 3, 2020, 5 pages, English translation.
First Office Action from corresponding Chinese Application No. 2017800197045, dated Feb. 6, 2020, 5 pages, in Chinese language.
First Office Action from corresponding Chinese Application No. 2017800197045, dated Feb. 6, 2020, 5 pages, English translation.
First Chinese Office Action, dated Mar. 2, 2020, pp. 1-11, Chinese Application No. 2017800201892, State Intellectual Property Office of P.R. China, in Chinese language.
First Chinese Office Action, dated Mar. 2, 2020, pp. 1-7, Chinese Application No. 2017800201892, State Intellectual Property Office of P.R. China, English Translation.
Chinese Search Report, dated Feb. 20, 2020, pp. 1-2, Chinese Application No. 2017800201892, State Intellectual Property Office of P.R. China, in Chinese language.
Second Japanese Office Action, dated Feb. 25, 2020, pp. 1-4, Japanese Application No. JP 2018-545873, Japanese Patent Office, in Japanese language.
Second Japanese Office Action, dated Feb. 25, 2020, pp. 1-4, Japanese Application No. JP 2018-545873, Japanese Patent Office, in English.
First Korean Office Action, dated Feb. 19, 2020, pp. 1-1, Korean Application No. 10-2018-7027789, Korean Intellectual Property Office, in Korean language.

(56) References Cited

OTHER PUBLICATIONS

First Korean Office Action, dated Feb. 19, 2020, pp. 1-10, Korean Application No. 10-2018-7027789, Korean Intellectual Property Office, in English.
Second Chinese Office Action, dated Jul. 1, 2021, pp. 1-6, Chinese Application No. CN 201780020189.2., State Intellectual Property Office of P.R. China, in Chinese.
Chinese Supplementary Search, dated Dec. 25, 2021, 1 page, Chinese Application No. CN 201780020189.2, State Intellectual Property Office of P.R. China, in Chinese language.
Chinese Supplementary Search, dated Jun. 27, 2021, pp. 1-2, Chinese Application No. CN 201780020189.2, State Intellectual Property Office of P.R. China, in Chinese language.
Chinese Supplementary Search, dated Sep. 27, 2020, pp. 1-2, Chinese Application No. CN 201780020189.2, State Intellectual Property Office of P.R. China, in Chinese language.
Third Chinese Office Action, dated Jul. 1, 2021, pp. 1-6, Chinese Application No. CN 201780020189.2, State Intellectual Property Office of P.R. China, in Chinese language.
Third Chinese Office Action, dated Jul. 1, 2021, pp. 1-8, Chinese Application No. CN 201780020189.2, State Intellectual Property Office of P.R. China, in English language.
Second Chinese Office Action, dated Oct. 10, 2020, pp. 1-10, Chinese Application No. CN 201780020189.2, State Intellectual Property Office of P.R. China, in Chinese language.
Second Chinese Office Action, dated Oct. 10, 2020, pp. 1-12, Chinese Application No. CN 201780020189.2, State Intellectual Property Office of P.R. China, in English language.
First Chinese Search, dated Jan. 21, 2020, 1 page, Chinese Application No. CN 201780019704.5, State Intellectual Property Office of P.R. China, in Chinese language.
Supplementary Chinese Search, dated Aug. 27, 2020, 1 page, Chinese Application No. CN 201780019704.5, State Intellectual Property Office of P.R. China, in Chinese language.
Japanese Search Report, dated Jun. 24, 2019, pp. 1-12, Japanese Application No. JP 2018-545873, Japanese Patent Office, in English language.
Japanese Search Report, dated Jun. 24, 2019, pp. 1-9 pages, Japanese Application No. JP 2018-545873, Japanese Patent Office, in Japanese language.
First Japanese Office Action, dated Sep. 24, 2019, pp. 1-5, Japanese Application No. JP 2018-545842, Japanese Patent Office, in English language.
First Japanese Office Action, dated Sep. 24, 2019, pp. 1-5, Japanese Application No. JP 2018-545842, Japanese Patent Office, in Japanese language.
Japanese Search Report, dated Aug. 29, 2019, pp. 1-17, Japanese Application No. JP 2018-545842, Japanese Patent Office, in English language.
Japanese Search Report, dated Aug. 29, 2019, pp. 1-17, Japanese Application No. JP 2018-545842, Japanese Patent Office, in Japanese language.
Third Japanese Office Action, dated Sep. 23, 2020, pp. 1-3, Japanese Application No. JP 2018-545842, Japanese Patent Office, in English language.
Third Japanese Office Action, dated Sep. 23, 2020, pp. 1-3, Japanese Application No. JP 2018-545842, Japanese Patent Office, in Japanese language.
First Japanese Office Action, dated Oct. 26, 2021, pp. 1-3, Japanese Application No. JP 2020-195283, Japanese Patent Office, in English language.
First Japanese Office Action, dated Oct. 26, 2021, pp. 1-3, Japanese Application No. JP 2020-195283, Japanese Patent Office, in Japanese language.
Japanese Search Report, dated Oct. 19, 2021, pp. 1-27, Japanese Application No. JP 2020-195283, Japanese Patent Office, in English language.
Japanese Search Report, dated Oct. 19, 2021, pp. 1-22, Japanese Application No. JP 2020-195283, Japanese Patent Office, Japanese language.
First Korean Office Action, dated Apr. 17, 2021, pp. 1-8, Korean Application No. KR 10-2021-7004020, Korean Intellectual Property Office, in English language.
First Korean Office Action, dated Apr. 17, 2021, pp. 1-6, Korean Application No. KR 10-2021-7004020, Korean Intellectual Property Office, in Korean language.
PCT International Search Report, dated Jul. 20, 2017, pp. 1-4, in PCT Application No. PCT/US2017/019851, European Patent Office, Rijswijk.
PCT Written Opinion of the International Searching Authority, dated Jul. 20, 2017, pp. 1-6, PCT Application No. PCT/US2017/019851, European Patent Office, Rijswijk.
European Office Action, dated Oct. 26, 2021, pp. 1-5, European Application No. EP17711411.3, European Office Action, Munich, Germany.
First Australian Office Action, dated Dec. 10, 2018, pp. 1-3, Australian Application No. AU2017227539, IP Australia.
First Australian Office Action, dated Dec. 10, 2018, pp. 1-5, Australian Application No. AU2017227540, IP Australia.
First Australian Office Action, dated Jun. 19, 2020, pp. 1-4, Australian Application No. AU2019268170, IP Australia.
Second Australian Office Action, dated May 20, 2021, pp. 1-3 pages, Australian Application No. AU2019268170, IP Australia.
Office Action from corresponding Japanese Application No. 2018-545873, dated Jul. 2, 2019, 4 pages, in Japanese language.

\* cited by examiner

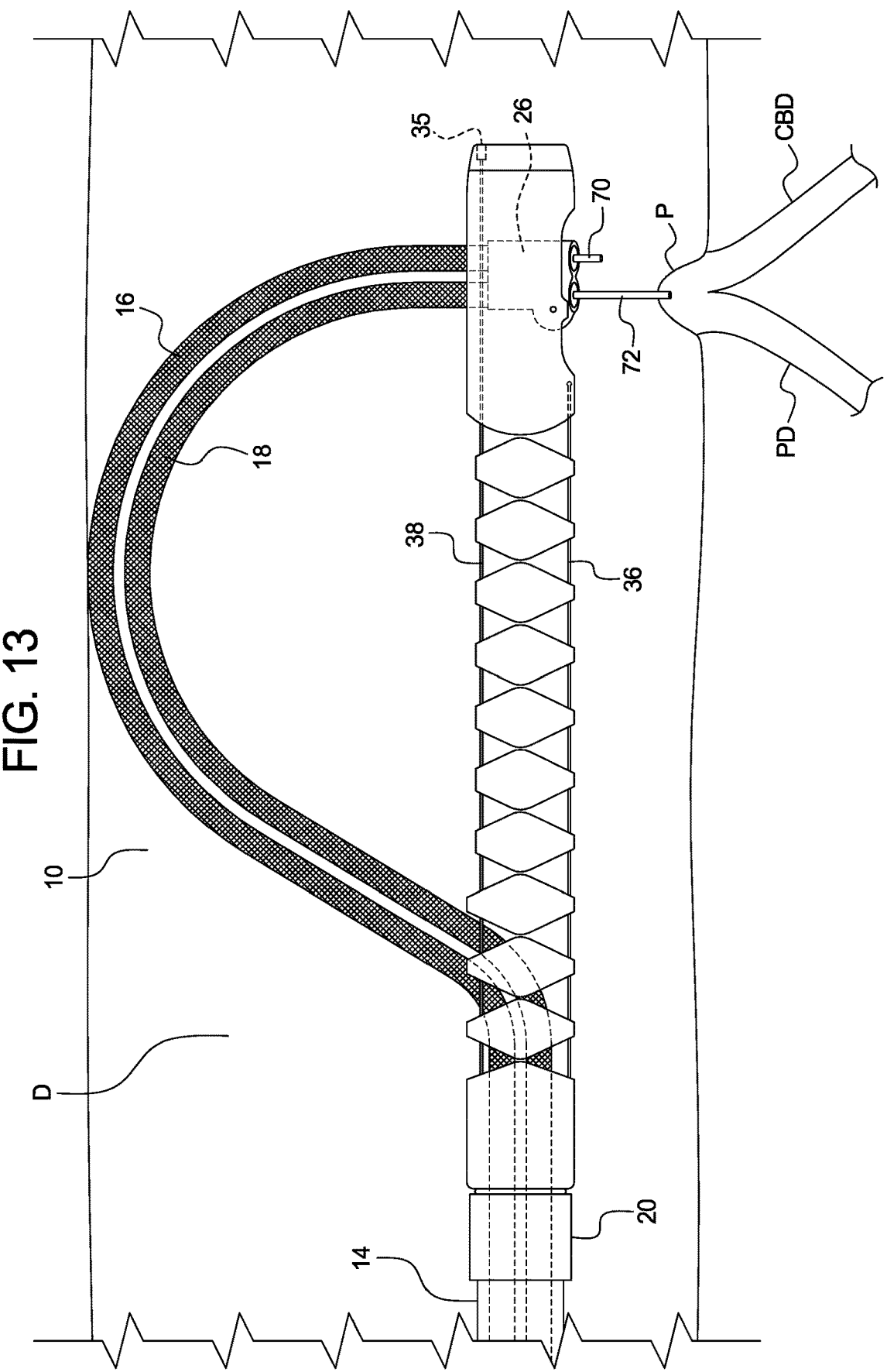

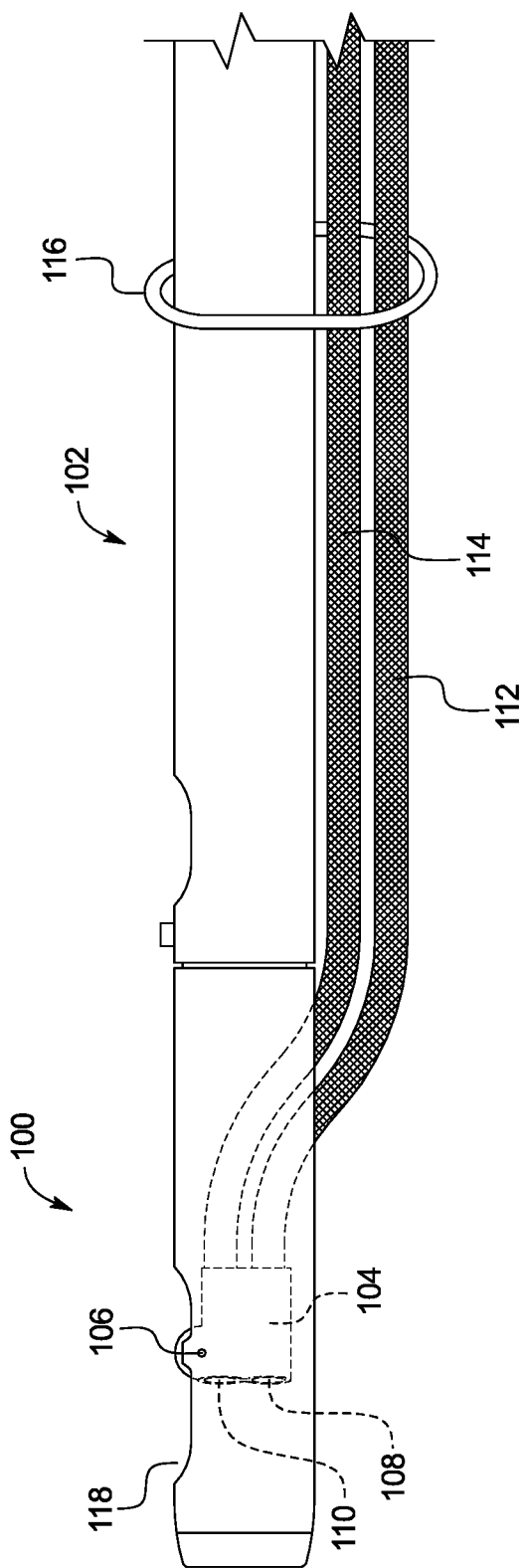

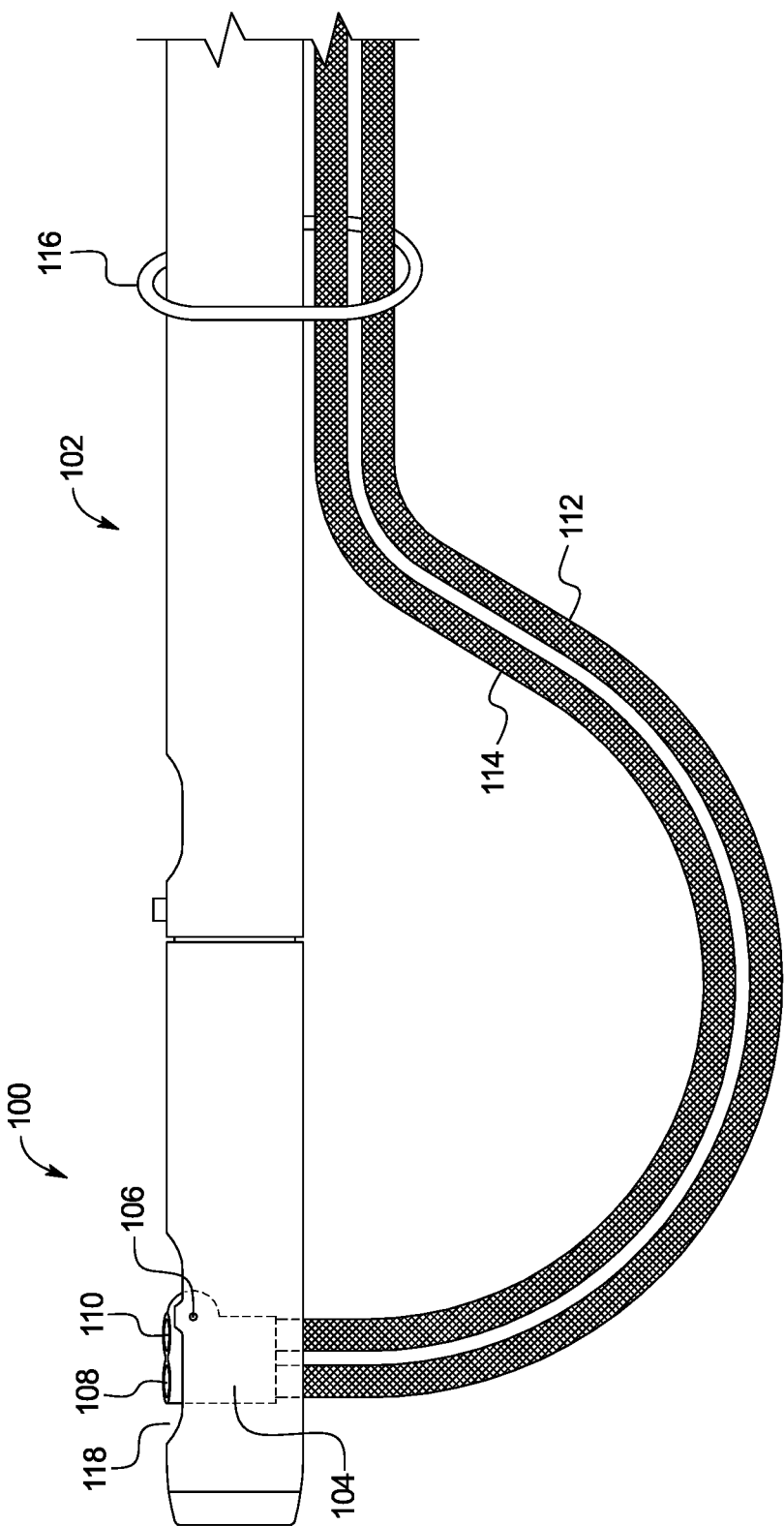

DEFLECTING ENDOSCOPE ACCESSORY CHANNELS

CROSS-REFERENCE TO RELATED APPLICATIONS

The present patent document claims the benefit of the filing date under 35 U.S.C. § 119(e) of Provisional U.S. Patent Application Ser. Nos. 62/382,552 filed Sep. 1, 2016 and 62/301,705 filed Mar. 1, 2016, which are hereby incorporated by reference.

FIELD

The present disclosure relates to medical devices and more specifically to endoscope systems.

BACKGROUND

The statements in this section merely provide background information related to the present disclosure and may not constitute prior art.

The duodenoscope is a medical device used in a variety of endoscopic procedures, including endoscopic retrograde cholangiopancreatography (ERCP). In an ERCP, a physician inserts the duodenoscope into a patient's mouth, through the patient's gastrointestinal (GI) tract, and into the duodenum until the distal end of the duodenoscope is positioned near the papilla of Vater, a small mound-like structure that acts as the entrance from the common bile duct and pancreatic duct into the duodenum. The physician then uses a variety of tools and accessories that are passed through a lumen in the duodenoscope to access the common bile duct or pancreatic duct through the papilla of Vater.

However, the duodenoscope suffers from several design issues. For example, due to the location of the papilla of Vater and shape of the duodenoscope, the endoscope tools or accessories must be bent sharply at (or sometimes more than) 90 degree angles at the distal end of the duodenoscope, which results in significant friction between the tools and duodenoscope and accompanying force transmission loss. Therefore, the accessories must be durable enough to withstand this sharp bend and the physician must apply a greater force to continue to advance the tools than is desired. Further, the built-in camera system of the duodenoscope is side-facing, making it difficult for novices and even experienced physicians to navigate the duodenoscope through the GI tract. Also, traditional duodenoscopes only have one accessory channel, making the use of multiple accessories time intensive and cumbersome. Additionally, duodenoscopes are difficult to clean, which may result in inadequate cleaning of the device after use and potential bacterial contamination of patients during subsequent use of the duodenoscope.

Therefore, it is desirable to have an endoscope system that eliminates or lessens the force transmission losses of traditional duodenoscopes. Further, increased and easier maneuverability of an endoscope system through and within the GI tract is desired. It is also desirable to provide an endoscope system that is easy to clean or is disposable.

SUMMARY

In one form of the present disclosure, a scope system is provided. The scope system comprises an elongate tube comprising a lumen extending therethrough, the elongate tube further comprising a distal portion. The scope system also comprises at least one accessory channel extending from a proximal end to a distal end and comprising an accessory lumen extending therethrough, the at least one accessory channel movably disposed at least partially within the lumen of the elongate tube, the at least one accessory channel comprising a distal section, the at least one accessory channel further comprising a forward-viewing configuration and a side-viewing configuration. Additionally, in the forward-viewing configuration, the distal section of the at least one accessory channel is substantially parallel to the distal portion of the elongate tube, and in the side-viewing configuration, the distal section of the at least one accessory channel is arced at a radius greater than a radius of the distal portion of the elongate tube.

In another aspect of the scope system, movement of the at least one accessory channel in a distal direction may move the at least one accessory channel from the forward-viewing configuration to the side-viewing configuration. Further, movement of the at least one accessory channel in a proximal direction may move the at least one accessory channel from the side-viewing configuration to the forward-viewing configuration. In the scope system, the distal portion may additionally comprise a pivot point, wherein during movement of the at least one accessory channel between the forward-viewing configuration and the side-viewing configuration, the at least one accessory channel rotates about the pivot point. Also, the at least one accessory channel may be biased towards the forward-viewing configuration or the side-viewing configuration. A pull member may be attached to the at least one accessory channel at a point distal the pivot point, wherein the pull member extends proximally from the point and wherein movement of the pull member in a proximal direction moves the at least one accessory channel from the forward-viewing configuration to the side-viewing configuration.

In yet another aspect of the scope system, the at least one accessory channel may comprise a first accessory channel and a second accessory channel, wherein the first accessory channel is movable between the forward-viewing configuration and the side-viewing configuration independent from the second accessory channel. Further, the first accessory channel may move between the forward-viewing configuration and side-viewing configuration in a different plane from where the second accessory channel moves between the forward-viewing configuration and the side-viewing configuration. In yet another aspect, the scope system may include a proximal link and a distal link, wherein the proximal link comprises a first end pivotally attached to the at least one accessory channel and a second end pivotally attached to the at least one accessory channel at a point distal the first end of the proximal link, wherein the distal link comprises a first end pivotally attached to the second end of the proximal link and a second end pivotally attached to the at least one accessory channel at a point distal the second end of the proximal link, wherein the second end of the distal link is also pivotally attached to the distal portion of the elongate tube, wherein during movement of the at least one accessory channel between the forward-viewing configuration and the side-viewing configuration, the links move with the at least one accessory channel.

In yet another aspect of the scope system, a rail may extend from a proximal end to a distal end, wherein the rail is pivotally attached to the at least one accessory channel at a first point, wherein the at least one accessory channel is longitudinally fixed with respect to the elongate tube at a second point proximal the first point, and wherein movement of the rail in a proximal direction moves the at least one accessory channel from the forward-viewing configuration to the side-viewing configuration. In another aspect, the scope system may include the distal portion of the elongate tube further comprising a slot extending longitudinally along the distal portion and the at least one accessory channel connected to the distal portion of the elongate tube via a pin slidably disposed within the slot, wherein a pull member extends proximally from the pin, wherein application of a proximally directed force to the pull member slides the pin proximally along the slot and moves the at least one accessory channel from the forward-viewing configuration to the side-viewing configuration.

In yet another aspect, the scope system may further comprise an inflatable balloon contacting the distal section of the at least one accessory channel, wherein the at least one accessory channel is pivotally connected to the distal portion of the elongate tube at a point distal the inflatable balloon, wherein inflation of the inflatable balloon moves the at least one accessory channel from the forward-viewing configuration to the side-viewing configuration.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 13 is another pictorial representation of an endoscope system in use;

FIG. 14 is a drawing of an endoscope cap in a forward-viewing configuration;

FIG. 15 is a drawing of an endoscope cap in a side-viewing configuration;

DETAILED DESCRIPTION

Figure 1:
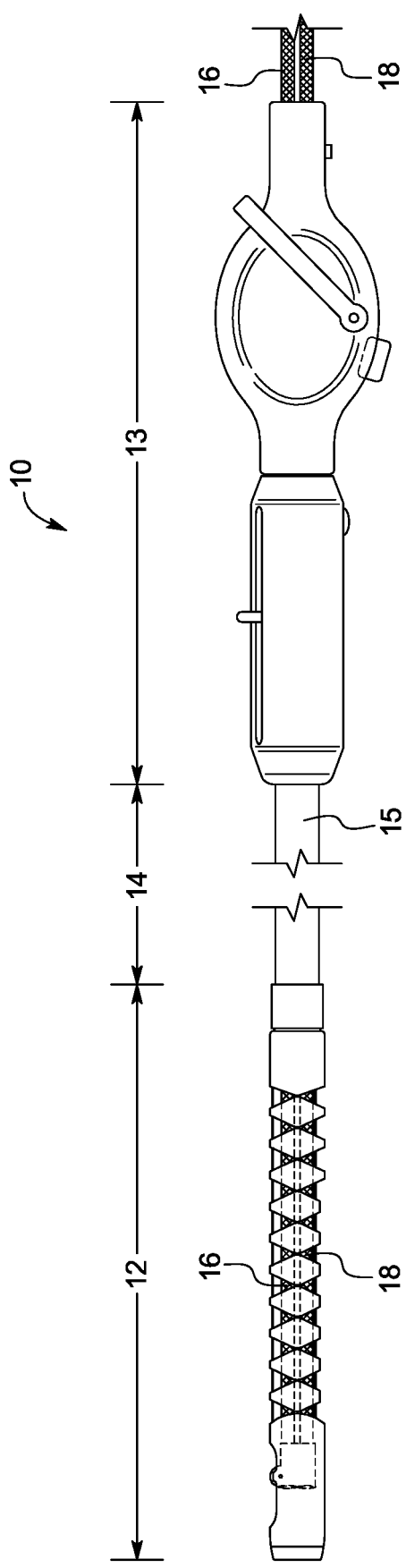
FIG. 1 is a drawing of an endoscope system.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

Referring to FIG. 1, an endoscope system 10 is provided. The endoscope system 10 may be generally shaped as an elongate tube including a distal portion 12, a central portion 14, and a proximal, or handle, portion 13. The central portion 14 may be a flexible, elongate tube with at least one lumen 15 running throughout the length of the central portion 14. The central portion 14 may connect the distal portion 12 and proximal portion 13 together. The lumen 15 of the central portion 14 may extend through the distal 12 and handle portions 13 of the endoscope system 10 as well. The central portion 14 may be made of a braided material such as pebax with a polytetrafluoroethylene liner to provide sufficient torqueability and pushability. Other potential materials for the central portion 14 include but are not limited to polyethylene, polypropylene, and nylon. The endoscope system 10 may further include two accessory channels 16, 18 each with lumens 17, 19 running therethrough (shown in FIG. 7). The accessory channels 16, 18 may be designed as individual elongated tubes that may be movable within the lumen 15 of the system 10, thus allowing longitudinal movement of the accessory channels 16, 18 with respect to the central portion 14. While this embodiment includes two accessory channels 16, 18, one or even three or more accessory channels may be used. For example, a single, larger accessory channel may be used to accommodate larger endoscopic tools. Further, in lieu of individual accessory channels 16, 18, a single elongate tube may be used with two or more lumens running through it. The accessory channels 16, 18 may range in diameter anywhere from 1 to 10 millimeters. In one exemplary embodiment, the first accessory channel 16 may be 4.2 millimeters in diameter while the second accessory channel 18 may be 3.7 millimeters in diameter. The accessory channels 16, 18 may extend proximally from or past the handle portion 13, through the lumen 15 and into the distal portion 12. Various tools, devices, and cameras may be inserted into and removed from the accessory channels 16, 18.

Figure 2:
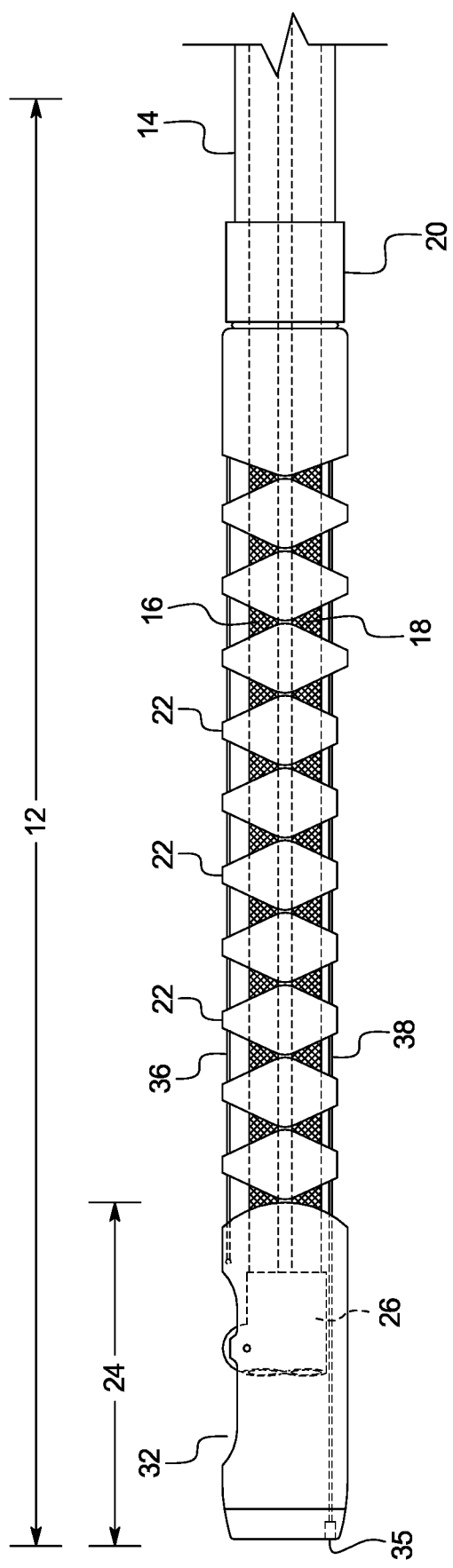
FIG. 2 is a detailed view of the distal portion of an endoscope system in a forward-facing configuration.

Now referring to FIG. 2, a detailed view of the distal portion 12 of the endoscope system 10 is shown. The endoscope system 10 may include a rotational bearing 20 disposed between the central portion 14 and the distal portion 12, which allows the distal portion 12 to rotate independently of the central portion 14. The distal portion 12 may have a flexible rib-like construction with multiple individual ribs 22 connected together to create an elongate tube with a lumen 15. These ribs 22 may be made of a variety of materials, such as polycarbonate, nylon, polyethylene, polypropylene, and polyoxymethylene. The accessory channels 16, 18 may travel through the ribs 22 to the distal end section 24 of the distal portion 12. The distal end section 24 may include a pivot arm 26 with first and second accessory lumens 28, 30 (shown in FIGS. 3 and 4). The distal ends of the accessory channels 16, 18 may be fixedly or movably disposed within respective accessory lumens 28, 30. The distal end section 24 may also include a side port 32 that provides access from the lumen 15 to a point external the endoscope system 10.

Figure 3:
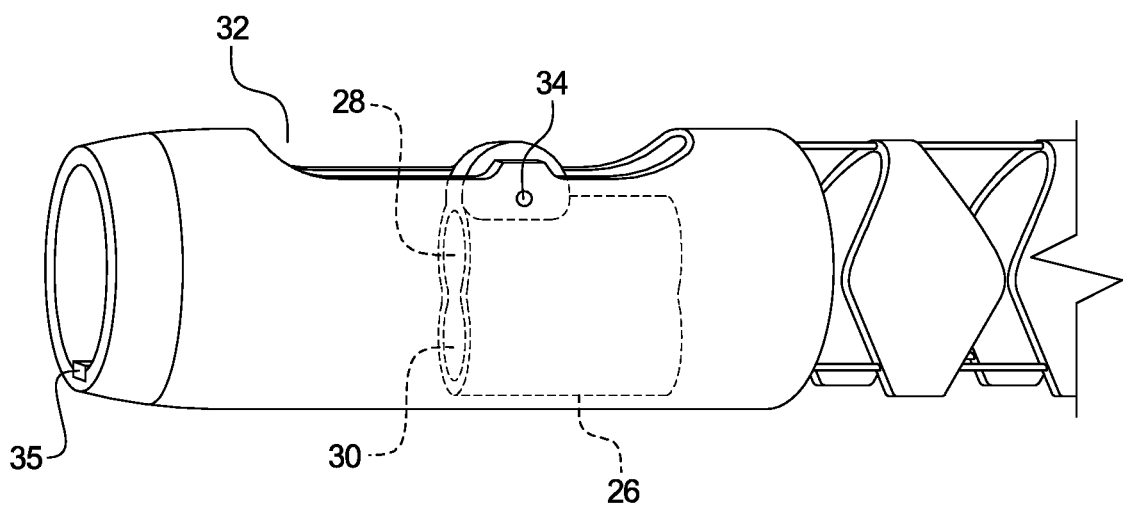
FIG. 3 is a detailed view of a pivot arm in a forward-facing configuration.
Figure 4:
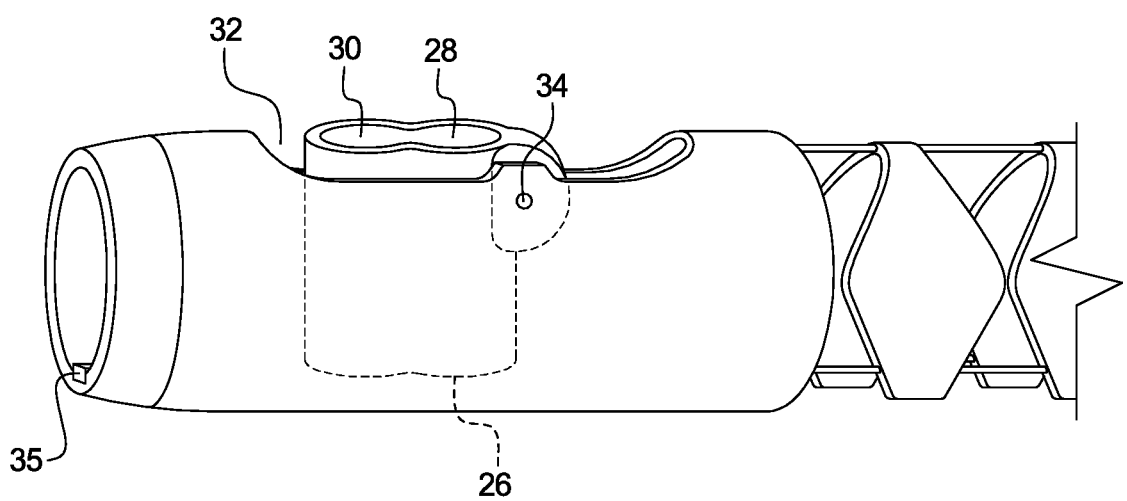
FIG. 4 is a detailed view of a pivot arm in a side-facing configuration.

The distal end section 24 of the distal portion 12 is shown in more detail in FIGS. 3 and 4. For clarity, the accessory channels 16, 18 are omitted from FIGS. 3 and 4. The pivot arm 26 may be connected to the distal end section 24 via a pin 34. The pin 34 may create a pivot point, around which the pivot arm 26 may rotate with respect to the distal end section 24 to the position shown in FIG. 4. The pivot arm 26 may be moved between a forward-viewing position as shown in FIG. 3 and a side-viewing position as shown in FIG. 4. A LED light 35 may be placed on the distal end section 24 to assist in navigation through a patient's GI tract. Alternatively, the LED light 35 may be placed at other locations on the distal end section 24, such as near the side port 32. Also, multiple LED lights 35 may be used at various locations on the system 10.

Figure 5:
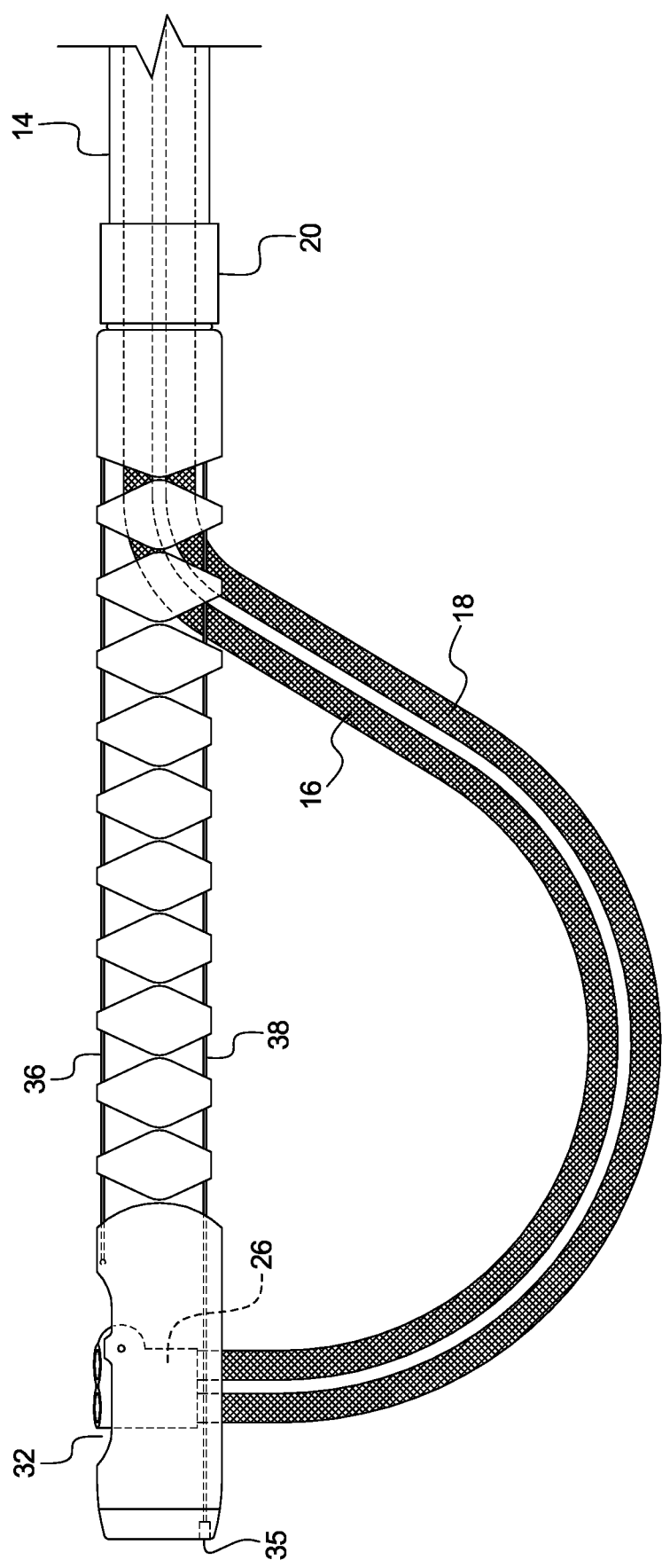
FIG. 5 is a detailed view of the distal portion of an endoscope system in a side-facing configuration.

As shown in FIGS. 2 and 5, the distal ends of the accessory channels 16, 18 may be secured to the pivot arm 26. Therefore, the accessory channels 16, 18 may rotate with the pivot arm 26 when moving the pivot arm 26 between the side-viewing and forward-viewing configurations. FIG. 2 shows the accessory channels 16, 18 in the forward-viewing configuration, while FIG. 5 shows the accessory channels 16, 18 in the side-viewing configuration. As can be seen in FIG. 5, when in the side-viewing configuration and due to the rotation of the pivot arm 26, distal portions of the accessory channels 16, 18 are bent outside of the confines of the ribs 22 and then curve back towards and into the pivot arm 26. Thus, in the forward-viewing configuration, the angle of curvature or bending radius of the distal portion 12 is the same as the angle of curvature of the accessory channels 16, 18 such that the accessory channels 16, 18 and the distal portion 12 of the scope system 10 are substantially parallel; but in the side-viewing configuration, the angle of curvature or bending radius of the accessory channels 16, 18 is greater than the angle of curvature of the distal portion 12 such that distal portions of the accessory channels 16, 18 extend outside the lumen 15 of the distal portion 12. To facilitate movement between the two configurations, the ribs 22 may have a U or V-shaped design with an open section that allows the accessory channels 16, 18 to move freely in and out of the ribs 22 (best shown in FIG. 7).

To move the pivot arm 26 from the forward-viewing position to the side-viewing position, the accessory channels 16, 18 may be pushed in a distal direction relative to proximal portion 13 and central portion 14, which applies a force through the accessory channels 16, 18 to the pivot arm 26. The resulting force causes the pivot arm 26 to rotate about the pivot point of the pin 34, thereby moving the accessory channels 16, 18 and pivot arm 26 into the side-viewing configuration. To move back to the forward-viewing configuration, a proximal force may be applied to the accessory channels 16, 18 relative to proximal portion 13 and central portion 14, thereby transferring the proximal force to the pivot arm 26. The proximal force then causes the pivot arm 26 to again rotate around the pivot point of the pin 34 in the opposite direction, thereby moving the accessory channels 16, 18 and the pivot arm 26 back to the forward-viewing configuration. To ensure that the accessory channels 16, 18 move in unison during these movements, the accessory channels 16, 18 may be secured together at any point along the length of the system 10, or even along the entire length. In one example, the accessory channels 16, 18 may be secured together using plastic tubing throughout the entire length of the central portion. In another example, the accessory channels 16, 18 may be secured together at the portions of the accessory channels 16, 18 that extend outside the constraints of the distal portion 12 when the system 10 is in the side-viewing configuration.

While this embodiment describes the use of a pivot arm 26 to assist in transferring the accessory channels 16, 18 between forward-viewing and side-viewing configurations, a variety of other methods and structures may be used. Further, rather than using a single pivot arm 26, multiple pivot arms may be used, or one for each accessory channel 16, 18. Therefore, each accessory channel 16, 18 may be moved between the forward-viewing and side-viewing configurations independently of each other. Further, the degree of rotation of the pivot arm 26 between the forward-viewing and side-viewing configuration may vary, potential ranging from 45 degrees to greater than 135 degrees.

Figure 6:
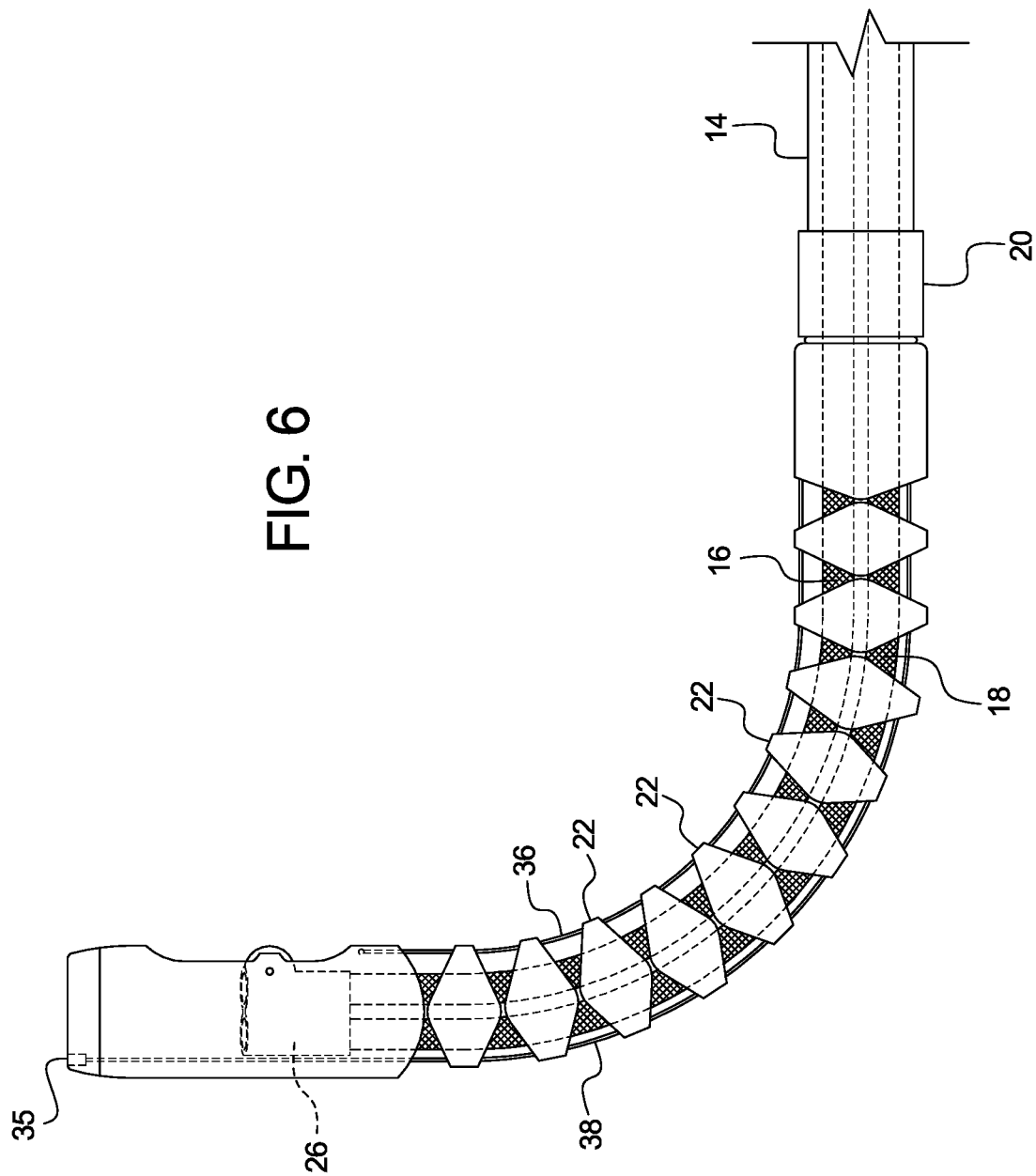
FIG. 6 is a detailed view of the distal portion of an endoscope system in a bent configuration.
Figure 7:
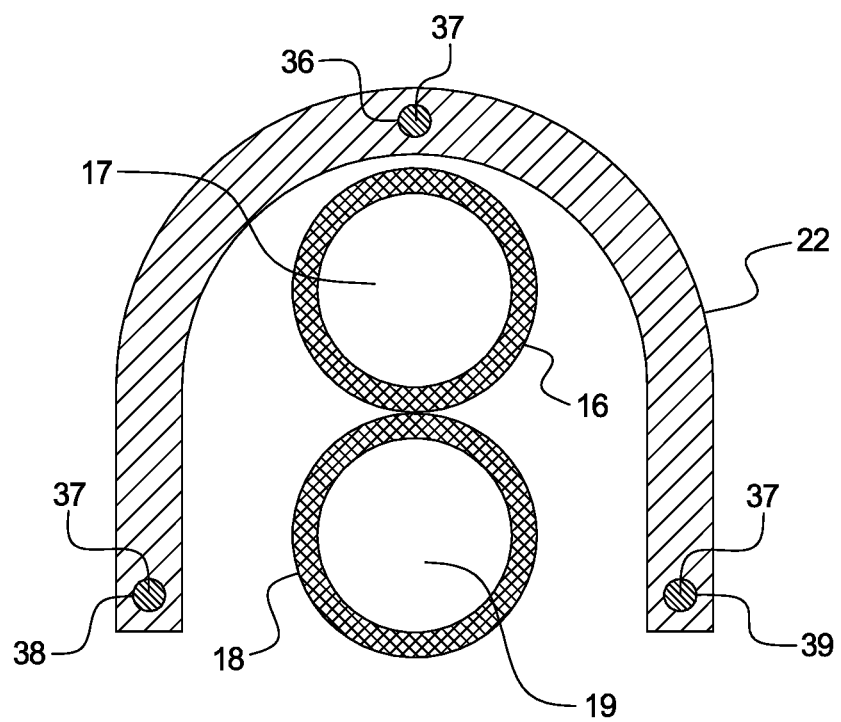
FIG. 7 is a cross-sectional view of a rib of an endoscope system.

In addition to the ability to switch between forward-viewing and side-viewing configurations, the distal portion 12 of the endoscope system 10 may also bend and rotate as desired. FIG. 2 shows the distal portion 12 in a straight configuration, while FIG. 6 shows the distal portion 12 in a bent configuration. The endoscope system 10 may include a first drive member 36, a second drive member 38, and a third drive member 39 (shown in FIG. 7). The second and third drive members 38, 39 may extend through the ribs 22 in the same plane of FIGS. 2 and 6, so only the second drive member 38 is representatively shown in those figures. FIG. 7 shows one potential orientation of the three drive members 36, 38, 39 in a cross-sectional view. The drive members 36, 38, 39 may be fixedly attached to the distal end section 24 and extend through, or outside of the lumen 15 to the handle portion 13. Alternatively, the drive members 36, 38, 39 may extend through dedicated low friction lumens or catheters along the length of the endoscope system 10 to the handle 13. The drive members 36, 38, 39 may also extend within the lumens of the accessory channels 16, 18. The first drive member 36 may be fixed on a wall of the distal end section 24 while the second and third drive members 38, 39 may be fixed on an opposing wall of the distal end section 24 with respect to the first drive member 36. To move the distal portion 12 from the straight configuration shown in FIG. 2 to the bent configuration shown in FIG. 6, the first drive member 36 may be pulled in a proximal direction. This proximal movement of the first drive member 36 may result in a force being applied through the first drive member 36 and to the distal end section 24. This force may cause the flexible, ribbed body of the distal portion 12 to bend towards the configuration shown in FIG. 6. To move the distal portion 12 back to the straight configuration, the second and third drive members 38, 39 may be pulled in a proximal direction. Since the second and third drive members 38, 39 are connected to the opposite side of the distal end section 24, a force is applied through the second and third drive members 38, 39 and to the distal end section 24 that may move the distal portion 12 back towards the straight configuration.

The drive members 36, 38, 39 may also be used to secure the individual ribs 22 of the distal portion 12 together, as shown in the cross-sectional view of an individual rib 22 in FIG. 7. The drive members 36, 38, 39 may run through small holes 37 in each individual rib 22, and sufficient tension may be applied to the drive members 36, 38, 39, thereby securing the ribs 22 together along the drive members 36, 38, 39. Due to this design, the ribs 22 may be shaped to allow for minimal contact between the individual ribs 22. For example, the ribs 22 shown in this embodiment have a substantially U-shaped cross-section with an opening and two sides. Each side of the ribs 22 may be diamond shaped when viewing the system 10 from a side angle (as best seen in FIGS. 3-4). The diamond shape reduces the contact points between each rib, thus minimizing friction and allowing for easier bending of the distal portion 12 to the bent configuration and maximum flexibility. Optionally, the second or third drive members 38, 39 may also include built-in electrical wiring that allows the second or third drive members 38, 39 to function as a circuit for the LED light 35 as well. Further, while this embodiment only describes the use of three drive members 36, 38, 39 more or less drive members may be used as desired. Alternatively or in addition to the drive members 36, 38, 39, the ribs 22 may be connected together using a variety of other methods, such as with mechanical hinges, adhesives, and other well-known devices. Further, additional elongate members may extend through the ribs 22 similar to the drive members 36, 38, 39 to provide additional support to the distal portion 12.

Additionally, the ribs 22 may be covered by a protective sleeve that may be made up of various biocompatible materials, such as an elastomeric material. The protective sleeve may protect the ribs 22 while also preventing body tissue from accidentally being pinched between the individual ribs 22 when the distal portion 12 is moved between the bent configuration and the straight configuration. The protective sleeve may also include a slot that corresponds to the openings in the ribs 22 that allows the accessory channels 16, 18 to move outside of the protective sleeve and between the forward-viewing configuration and the side-viewing configuration. The protective sleeve may also help with torque transmission when moving the distal portion 12 between the bent and straight configurations. Some natural lag may occur when manipulating the drive members 36, 38, 39 that may cause part of the distal portion 12 to move first, while the rest of the distal portion lags behind, but eventually moves as well. The protective sleeve may ensure that the entire distal portion 12 moves together and with minimal lag.

Figure 8:
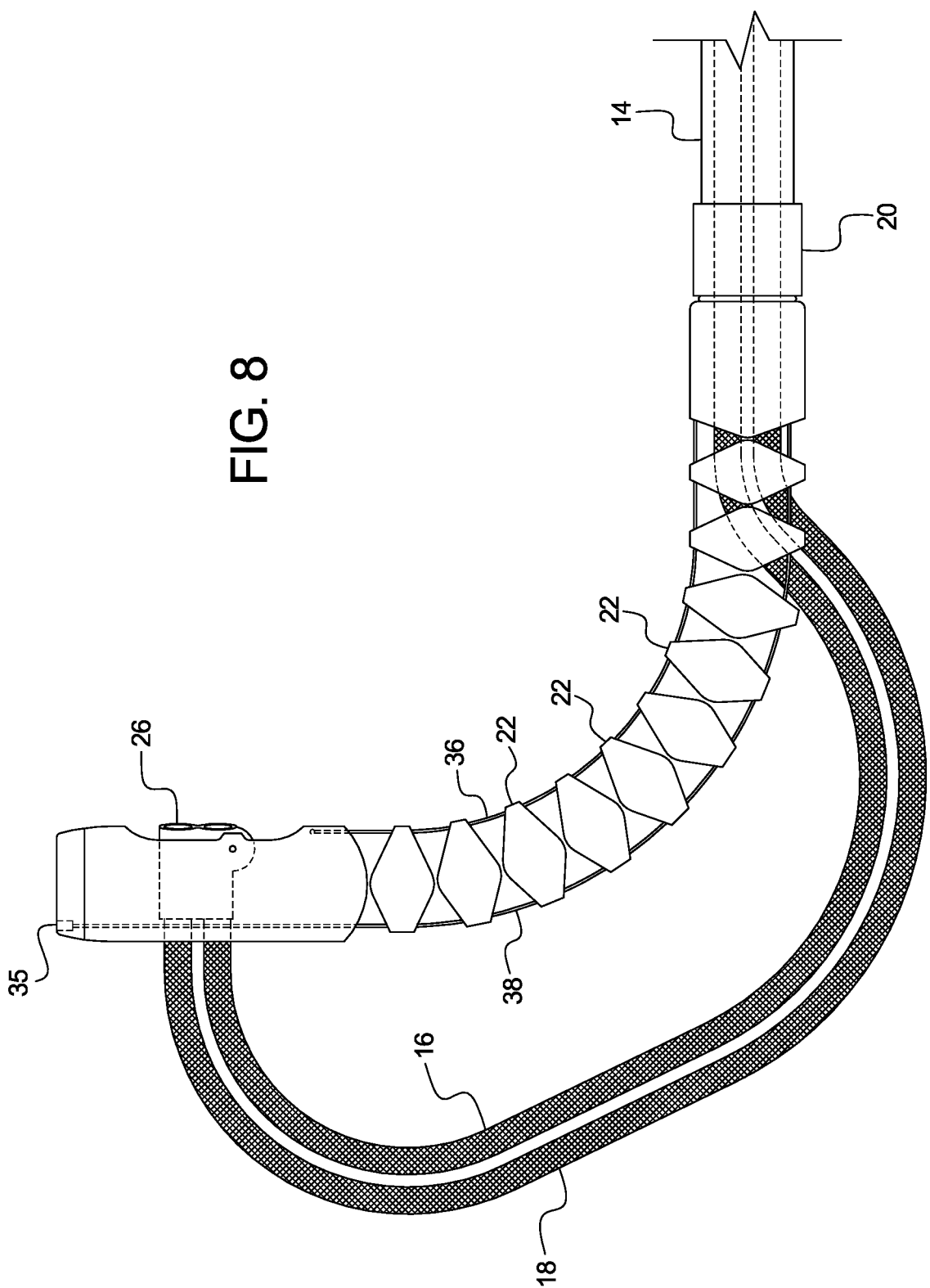
FIG. 8 is a detailed view of the distal portion of an endoscope system in a bent and side-facing configuration.

The endoscope system 10 may move between a bent configuration and a straight configuration while the endoscope system 10 is also in either the forward-facing or side-facing configurations. For example, FIG. 8 shows the endoscope system 10 in a bent and side-facing configuration. The endoscope system 10 can be manipulated and used in any combination of the above mentions configurations, and may be repeatedly movable between all configurations.

The accessory channels 16, 18 may be used to provide access for a variety of medical tools and accessories through the endoscope system 10 and into a patient's body. For example, a camera system may be inserted into one of the accessory channels 16 while a variety of tools such as forceps, sphincterotomes, wires, dilation balloons, extraction balloons, stents, needle knives, hemostasis clips, and any other catheter based tool may be inserted into the second accessory channel 18. The tools may be advanced past the distal ends of the accessory channels 16, 18 where they may be used to operate on a patient.

Figure 9:
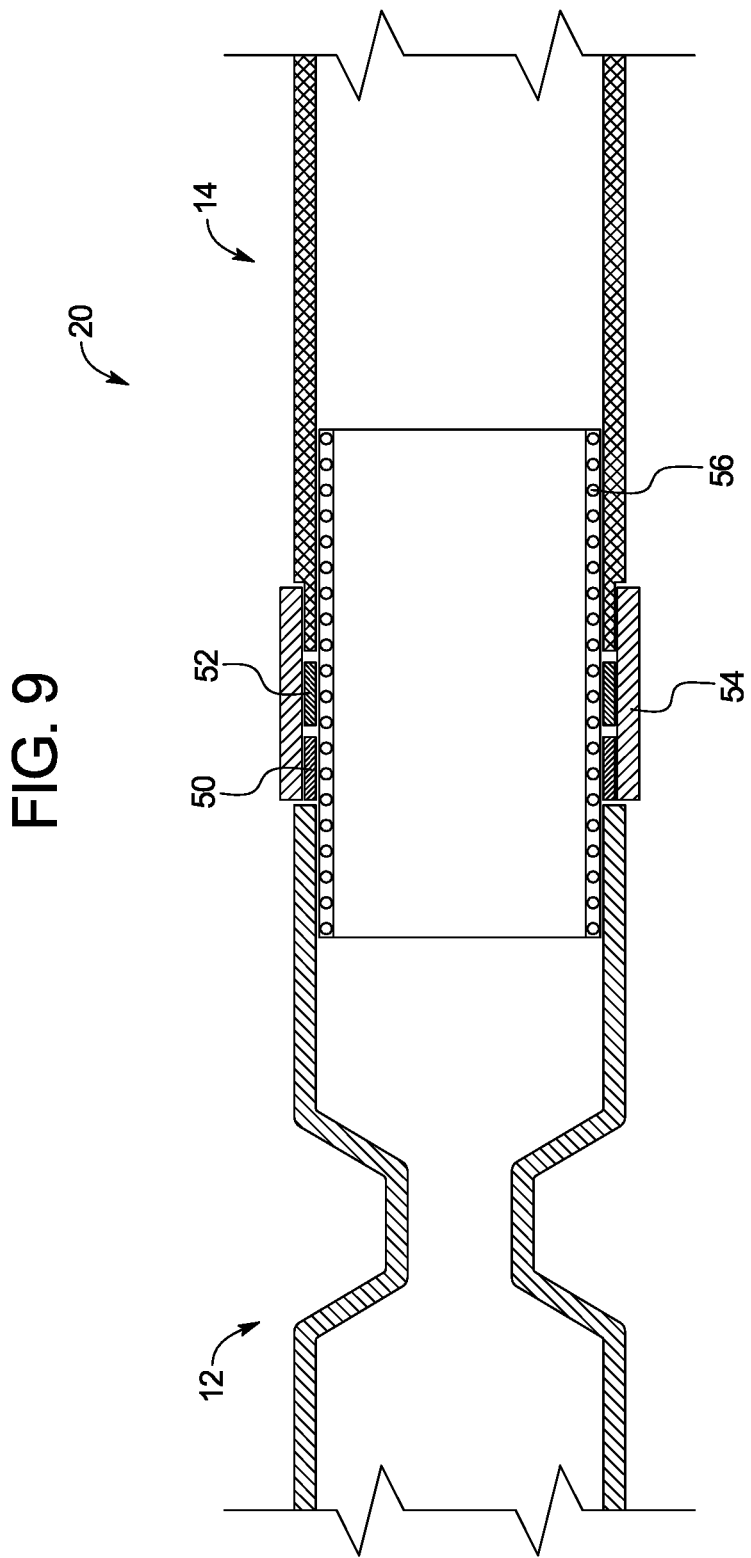
FIG. 9 is a detailed view of an axially rotatable bearing of an endoscope system.

FIG. 9 shows a cross-sectional view of the axially rotatable bearing 20 and its functionality. The axially rotatable bearing 20 may include a first ring 50 and a second ring 52. The axially rotatable bearing 20 may further include a first tube 54 and a second tube 56. The first tube 54 may be fixedly attached to the central portion 14 and the first ring 50. The second tube 56 may be fixedly attached to the distal portion 12 and the second ring 52. The first tube 54 and first ring 50 may be freely rotatable with respect to the second tube 56 and second ring 52, thereby making the distal portion 12 freely rotatable with respect to the central portion 14. Since the first ring 50 is indirectly secured to the central portion 14, but is located distal the second ring 52 which is indirectly secured to the distal portion 12, the distal portion 12 and central portion 14 may remain secured to each other while still remaining freely rotatable with respect to each other. The distal portion 12 may be freely rotated when the endoscope system 10 is in any one of the configurations described above, including forward-facing, side-facing, straight, and bent configurations. The accessory channels 16, 18 and the drive members 36, 38, 39 may pass freely through the lumen 15 of the bearing with causes no or minimal interference to the bearing 20. This is merely one potential design for the axially rotatable bearing 20, and various other designs that allow free rotation of the distal portion 12 with respect to the central portion 14 may be used.

Figure 10:
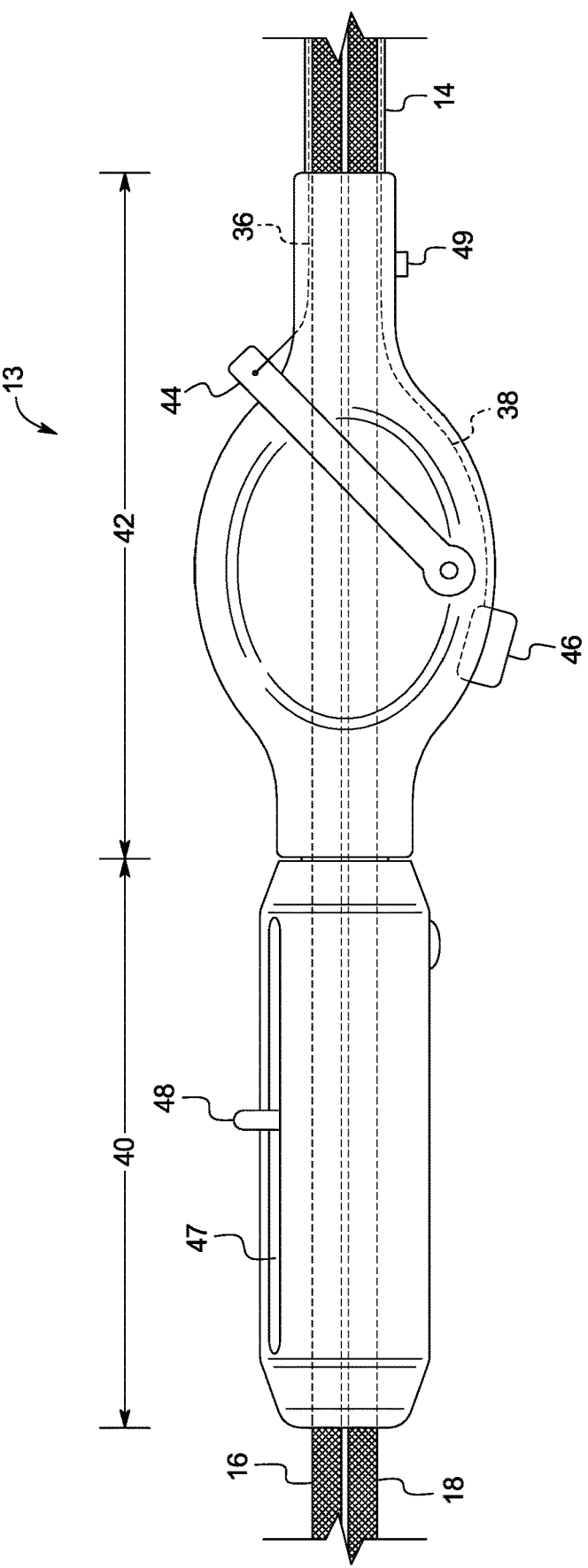
FIG. 10 is a detailed view of a handle of an endoscope system.

Now referring to FIG. 10, a detailed view of the handle portion 13 of the endoscope system 10 is shown. The handle 13 may include several controls used to manipulate the distal portion 12 of the endoscope system 10. The handle 13 may be include a first portion 40 and a second portion 42, where the first portion 40 is freely rotatable with respect to the second portion 42. The handle 13 may include an arm 44 that is connected to the first drive member 36, which is further connected to the distal end section 24. The arm 44 may be moved and/or pivoted in a proximal direction, which causes the first drive member 36 to be pulled in a proximal direction, thereby applying a proximal force to the distal end section 24 and causing the distal portion 12 to bend as shown in FIG. 6. The handle 13 may further include a first slider 46, which may be connected to the second and third drive member 38, 39, which is further connected to the distal end section 24. Similarly to the arm 44, the first slider 46 may be moved in a proximal direction which results in a proximal force being applied to the distal end section 24 through the second and third drive members 38, 39, thereby causing the distal portion 12 to bend back towards, and even past, the position shown in FIG. 2.

The handle 13 may further include a second slider 48, which may be slid along a slot 47 in a proximal and distal direction. The second slider 48 may be connected to the first and second accessory channels 16, 18, where proximal or distal movement of the second slider 48 causes corresponding movement of the first and second accessory channels 16, 18. Therefore, moving the second slider 48 in a distal direction causes the accessory channels 16, 18 to move in a distal direction, thereby causing the pivot arm 26 to rotate and move into the side-viewing configuration. Further, moving the second slider 48 in a proximal direction causes the pivot arm 26 to rotate back towards the forward-viewing configuration. Also, as discussed earlier, the first portion 40 may be rotated freely with respect to the second portion 42. Since the accessory channels 16, 18 are fixed to the second slider 48, rotation of the first portion 40 may cause corresponding rotation of the accessory channels 16, 18. Since, the accessory channels 16, 18 are also fixed at their distal ends to the pivot arm 26, which is in turn fixed to the rest of the distal portion 12 of the system 10, rotation of the first portion may cause corresponding rotation of the entire distal portion 12. Further, since the axially rotatable bearing 20 as shown in FIG. 9 is disposed between the distal portion 12 and central portion 14, the distal portion 12 may rotate in response to rotation of the first portion 40 of the handle 13 without the rest of the system 10 rotating. Additionally, a knob 49 may be used to control the brightness or power of the LED light 35, which is wired to the knob 49 at least partially through the second and/or third drive members 38, 39.

The handle 13 is merely one potential embodiment of the handle portion 13, and any other handle design capable of controlling the endoscope system 10 may be used, including variations on the arms or sliders that control various features of the system 10. For example, the handle 13 and various controls such as the arm 44 and sliders 46, 48 may include locking elements that lock the system in the various aforementioned configurations. In one example, the handle 13 may include frictional locks, where the various arms and sliders may be maintained in their current position with a frictional force. However, the application of an external force may still move the controls as desired. In another alternative handle 13 design, the arm 44 may have a pivot point in the center of the handle, with one end of the arm 44 connected to the first drive member 36 and the other end of the arm 44 connected to the second and third drive members 38, 39, thus allowing the arm 44 to control both directions of bending motion for the distal portion 12.

Figure 11:
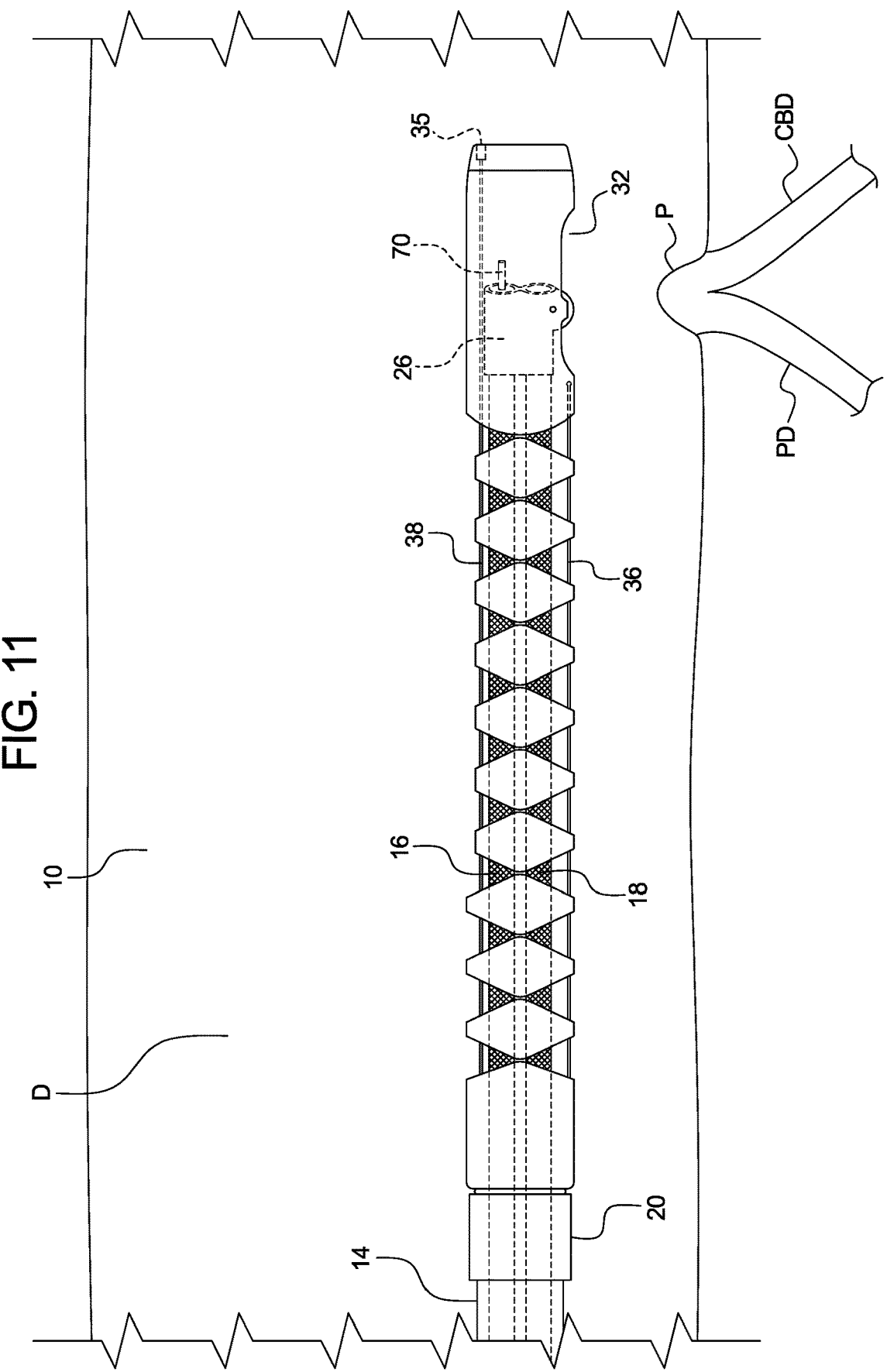
FIG. 11 is a pictorial representation of an endoscope system in use.

The endoscope system 10 described herein may be used for a variety of medical procedures. However, one such procedure, an endoscopic retrograde cholangiopancreatography (ERCP), is now described with reference to FIGS. 11-13. The endoscope system 10 may be inserted into a patient's mouth and through the gastrointestinal tract. It may be preferable to insert the endoscope system 10 in the forward-facing position, which provides a lower profile than the side-facing position, thus making advancement through the gastrointestinal tract easier. Further, a camera system 70 may be inserted into one of the accessory channels 16 to assist the physician in guiding the endoscope system 10 through the patient's gastrointestinal tract. The camera system 70 may be integral with the accessory channel 16, or it may be advanceable past the distal end of the accessory channel 16. Further, the camera system 70 may include a light source independent of the rest of the system 10. The camera system 70 may be positioned in the accessory channel 16 such that the distal end of the camera system extends into or just past the pivot arm 26, thus providing a clear view of the distal end of the endoscope system 10 as it is advanced. The endoscope system 10 may be advanced past the stomach and into the duodenum D until the distal end section 24 is disposed near the papilla of Vater P as shown in FIG. 11.

Figure 12:
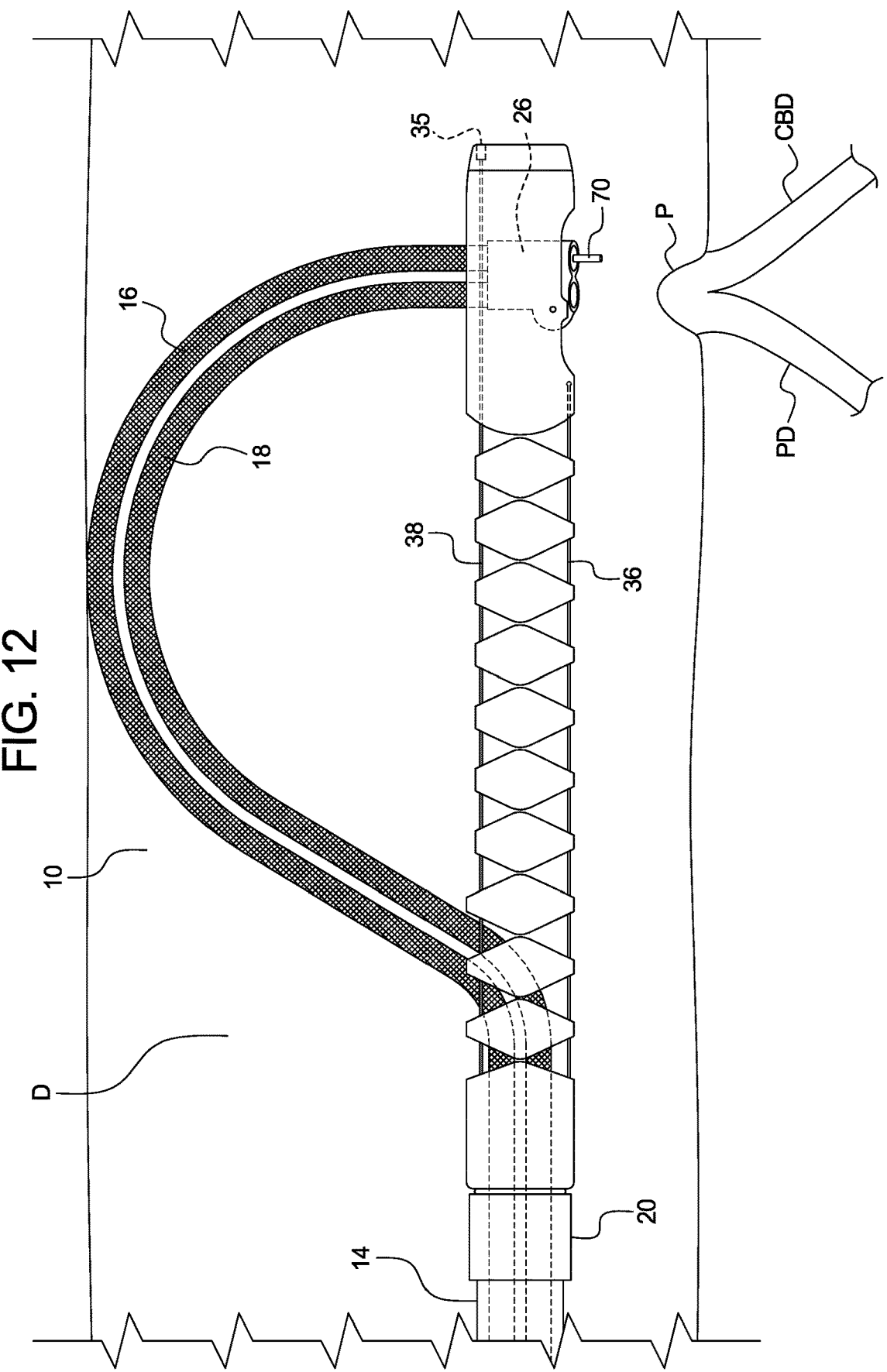
FIG. 12 is another pictorial representation of an endoscope system in use.

Once the distal end section 24 is disposed near the papilla of Vater P, the distal portion 12 may be bent or straightened using the arm 44 and first slider 46 of the handle 13 until the distal end section 24 is substantially perpendicular to the papilla of Vater P. The distal portion 12 may further be rotated by the first portion 40 of the handle 13 so that the side port 32 is aimed towards the papilla of Vater P. The accessory channels 16, 18 may next be moved from the forward-facing configuration to the side-facing configuration by moving the second slider 48 of the handle 13 in a distal direction until the pivot arm 26 rotates to the side-facing configuration. The distal portion 12 may be further manipulated by the controls of the handle 13 until the distal end section 24 is properly positioned with relation to the papilla of Vater P as shown in FIG. 12. In this position, the accessory channels 16, 18 have a direct and straight line of access to the papilla of Vater P. FIG. 12 further shows at least one of the accessory channels 16, 18 contacting the wall of the duodenum D opposite the papilla of Vater P. This contact helps push the entire endoscope system 10 closer to the papilla of Vater P and provides an anchor point to help secure the endoscope system 10 within the duodenum or other target portion of the anatomy.

At this point, a variety of tools may be used to access the pancreatic duct D or the common bile duct C through the papilla of Vater P. If a camera system 70 was used previously, it may optionally be removed to allow for additional tools to be used. The gradual, curved path of the accessory channels 16, 18 may reduce friction between the accessory channels 16, 18 and tools, thus reducing the amount of force required for the physician to advance the tools towards the papilla of Vater P. For example, the sphincter of Oddi, a strong muscle found within the papilla of Vater P, may need to be dilated or cut to allow access into the common bile duct CBD or pancreatic duct PD. Therefore, a sphincterotome 72, a long tool with a thin wire capable of cutting through the sphincter of Oddi, may be advanced through the accessory channel 18 and towards the papilla P as shown in FIG. 13. The sphincterotome 72 may then be used to cut into the sphincter of Oddi, therefore creating an access point into the common bile duct CBD and pancreatic duct PD. Physicians often have difficulty properly positioning the sphincterotome 72 or other dilation tools towards the sphincter and providing sufficient force to the sphincter. The accessory channels 16, 18 contacting the opposite wall of the duodenum D provides an anchor point that may allow the physician to apply a sufficient amount of force to the sphincterotome 72 or other tools without fear of losing positioning of the endoscope system 10. Once an access point has been created, a variety of tools, including the camera system 70, radiopaque dye injector, kidney stone retriever, etc. may be advanced through either of the accessory channels 16, 18 and into the common bile duct CBD or pancreatic duct PD.

Following completion of the procedure, the various tools used may be withdrawn and the endoscope system 10 may be moved to the straight configuration and the forward-viewing configuration, thus permitting the physician to remove the endoscope system 10 from the patient's body in substantially the same was as it was inserted.

In a second embodiment shown in FIG. 14, a scope cap 100 may be attachable to a standard duodenoscope or endoscope. The scope cap 100 has many of the features of the aforementioned embodiments. The scope cap 100 may be removably or fixedly attached to a duodenoscope 102 using a variety of methods, including a friction fit, elastic belt, and adhesives. Alternatively, the scope cap 100 may be attached to an endoscope, cholangioscope, or any other similar devices. The endoscope cap 100 may include a pivot arm 104. The pivot arm 104 may be similar to the pivot arm described in previous embodiments, with a pin 106 creating a pivot point around which the pivot arm 104 may rotate with respect to the rest of the scope cap 100. The pivot arm 104 may further include a first pivot lumen 108 and a second pivot lumen 110. A first accessory channel 112 and a second accessory channel 114, each with respective lumens, may be connected to the respective pivot lumens 108, 110. The accessory channels 112, 114 may run from the pivot arm 104, along the outside of the duodenoscope 102, and to or near the proximal end of the duodenoscope 102. Multiple clips 116 (only one shown in FIG. 14) may be used to secure the accessory channels 112, 114 to the duodenoscope 102. The clips 116 may be spaced apart the entire length of the duodenoscope 102, thus ensuring that the accessory channels 112, 114 do not separate significantly from the duodenoscope 102. It may be ideal for the clips 116 to still permit longitudinal movement of the accessory channels 112, 114 along the length of the duodenoscope 102, while restricting or limiting other movement. For example, clips 116 may be fixedly connected to accessory channels 112, 114, and slidably connected to the scope 102. While clips 116 are used in this example, a variety of other attachment methods may be used such as loops or rings that may be slide along the length of the duodenoscope 102 to a desired location.

The scope cap 100 may move between a forward-viewing configuration as shown in FIG. 14 and a side-viewing configuration as shown in FIG. 15. To move the scope cap 100 from the forward-viewing configuration to the side-viewing configuration, the accessory channels 112, 114 may be advanced in a distal direction with respect to the duodenoscope 102 and scope cap 100. This movement results in a force being applied to the pivot arm 104, thereby causing the pivot arm 104 to rotate about the pivot point 106 and thereby move the scope cap 100 into the side-viewing configuration as shown in FIG. 15. In the side-viewing configuration, the pivot arm 104 may be rotated about 90 degrees in comparison to the forward-viewing configuration, while the accessory channels 112, 114 may bend away from the duodenoscope 102 and then bend back towards the scope cap 100 substantially perpendicular to the length of the duodenoscope 102. Alternatively, the pivot arm 104 may be rotated at a variety of angles, potentially ranging anywhere from 45 degrees to greater than 135 degrees. To facilitate this bend or arch, it may be ideal to provide a sufficient amount of space between the most distal clip 116 and the scope cap 100, thus permitting the accessory channels 112, 114 to bend away from the duodenoscope between the most distal clip 116 and scope cap 100 with minimal restriction. When in the side-viewing configuration, an opening 118 in the scope cap 100 may permit tools or accessories passed through the accessory channels 112, 114 to be advanced past the scope cap 100.

In use, the scope cap 100 may be used in an ERCP procedure in a manner similar to the embodiments described above. The scope cap 100 may be preinstalled to a duodenoscope 102 or other scope, or a physician or other operator may attach the scope cap 100 and accessory channels 112, 114 to any standard, existing scope. The scope cap 100 may be attached to the distal end of the duodenoscope 102, while the clips 116 may be used to secure the accessory channels 112, 114 to the outside of the duodenoscope 102. The duodenoscope 102, along with the scope cap 100 and accessory channels 112, 114, may then be inserted into a patient's mouth in the forward-viewing configuration and advanced through the gastrointestinal tract until the scope cap 100 is positioned near the papilla of Vater. The accessory channels 112, 114 may then be advanced distally so as to cause the pivot arm 104 to rotate about the pivot point 106 and to the side-viewing configuration. Various accessories or tools may then be advanced through the accessory channels 112, 114 and used as desired.

The endoscope system 10 and scope cap 100, or any portions thereof, may be designed to be disposable, thus reducing the risk of bacterial infection due to incomplete cleaning between uses.

As mentioned above, the pivot arm 26 may be replaced or supplemented with a variety of other components to assist in moving the accessory channels 16, 18 between forward-viewing and side-viewing configurations. FIGS. 16A through 22B show several additional exemplary embodiments that move the accessory channels 16, 18 between forward-viewing and side-viewing configurations in various ways. While several of the embodiments show a single accessory channel for simplicity, these embodiments are not so limited and may have multiple accessory channels.

Figure 16A:
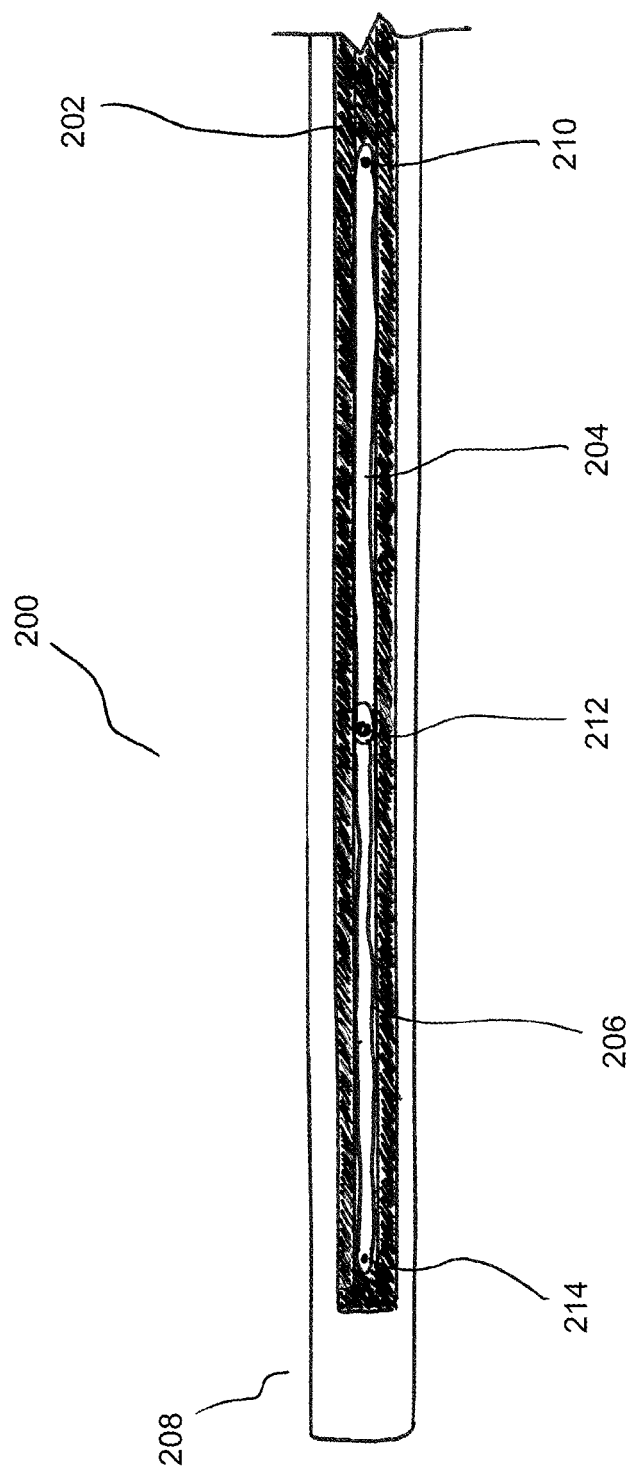
FIG. 16A is an alternative embodiment of an endoscope system in a forward-viewing configuration.
Figure 16B:
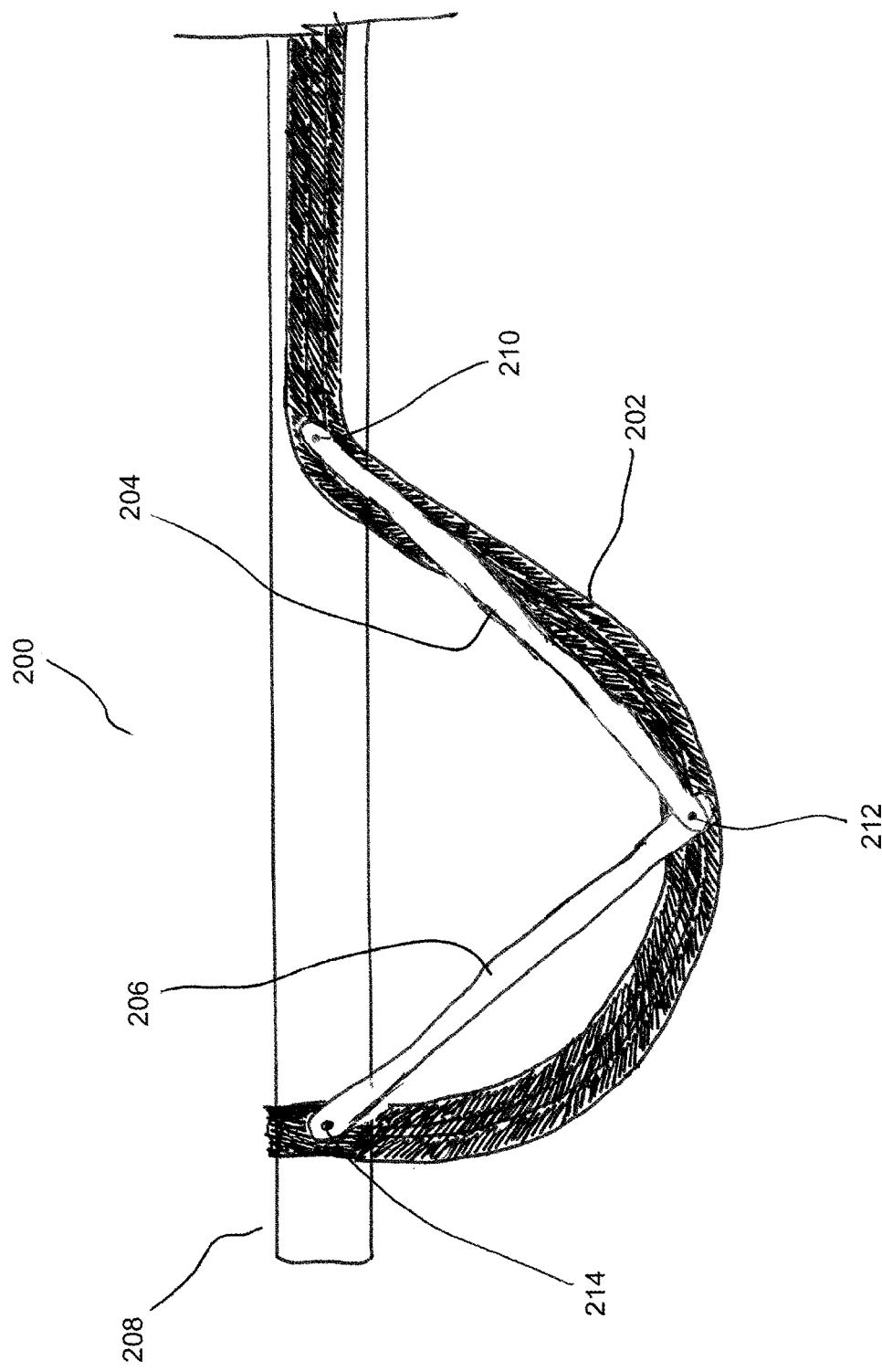
FIG. 16B is an alternative embodiment of an endoscope system in a side-viewing configuration.

FIGS. 16A and 16B show a distal portion 208 of an endoscope system 200 having an accessory channel 202. FIG. 16A shows the accessory channel 202 in a forward-viewing configuration and FIG. 16B shows the accessory channel 202 in a side-viewing configuration. Two links, a proximal link 204 and a distal link 206 may be attached at various points to the distal portion 208 of the endoscope system 200 and the accessory channel 202. In this embodiment, one end of the proximal link 204 is pivotally attached to the accessory channel 202 via a pin 210 while the other end of the proximal link 204 is pivotally attached to one end of the distal link 206 and the accessory channel 202 via another pin 212. The other end of the distal link 206 may then be pivotally attached to the distal portion 208 of the endoscope system 10 and the distal end of the accessory channel 202 via another pin 214, or some other pivoting structure such as the pivot arm described in previous embodiments. To move the accessory channel 202 from the forward-viewing configuration to the side-viewing configuration, a distally directed force may be applied to the accessory channel 202, which causes the accessory channel 202 to slide distally with respect to the distal portion 208 of the endoscope system 10 while the distal end of the accessory channel 202 also pivots around the pin 214. As the accessory channel 202 slides distally, the links 204, 206, which are ideally rigid or semi-rigid, bend away from the distal portion 208, thereby also bending a portion of the accessory channel 202 as shown in FIG. 16B. The accessory channel 202 can be moved back to the forward-viewing configuration by applying a proximally directed force to the accessory channel 202. Alternatively, the accessory channel 202 may be moved to the side-viewing configuration by a device that forces the links 204, 206 away from the distal portion 208 of the endoscope system 10, such as a biasing force or pull wire. The links 204, 206 may provide support to the accessory channel 202 and help guide or control the shape of the accessory channel 202 as it is moved to the side-viewing configuration. The lengths of the links 204, 206 can be altered to alter the shape of the accessory channel 202. For example, making the proximal link 204 longer than the distal link 206 may induce a greater bend towards the distal end of the accessory channel 202. Further, three, four, or even more links may be used to create a potentially create a linkage with more kinematic advantages. If more than one accessory channel is used in the endoscope system 10, separate links may be used to individually manipulate each accessory channel between the forward and side-viewing configurations. Alternatively, a single system of links (including more than two links), or linkage, may be used to manipulate multiple accessory channels together.

Figure 17A:
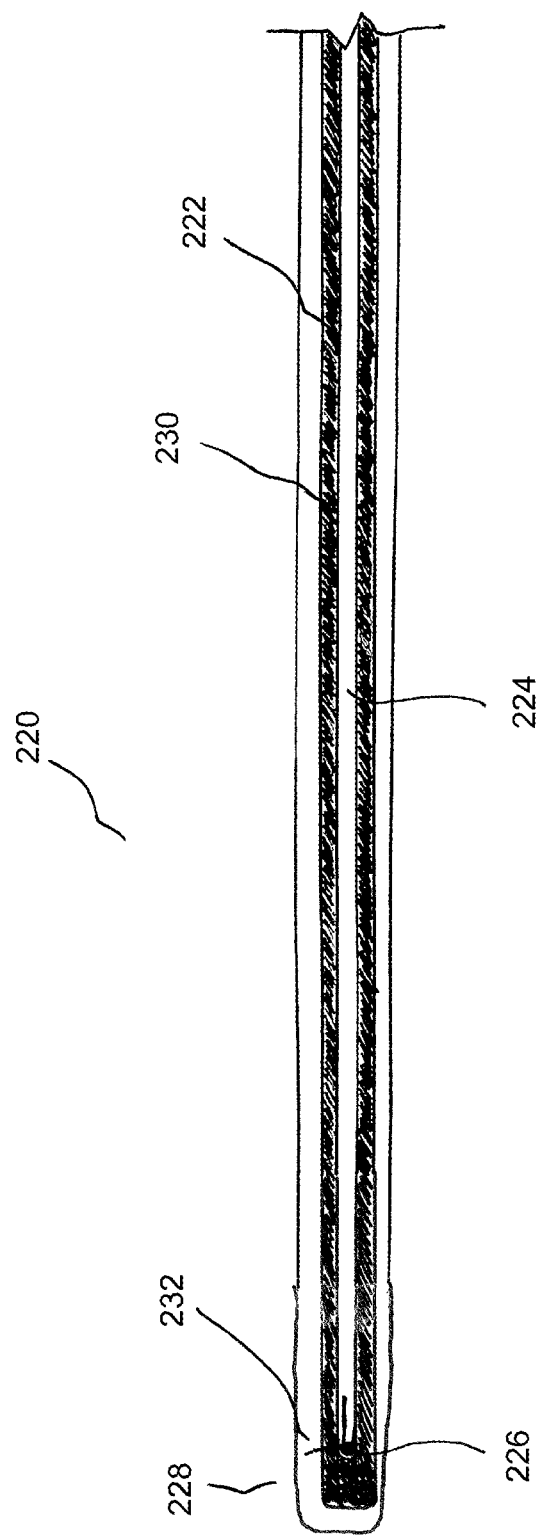
FIG. 17A is another alternative embodiment of an endoscope system in a forward-viewing configuration.
Figure 17B:
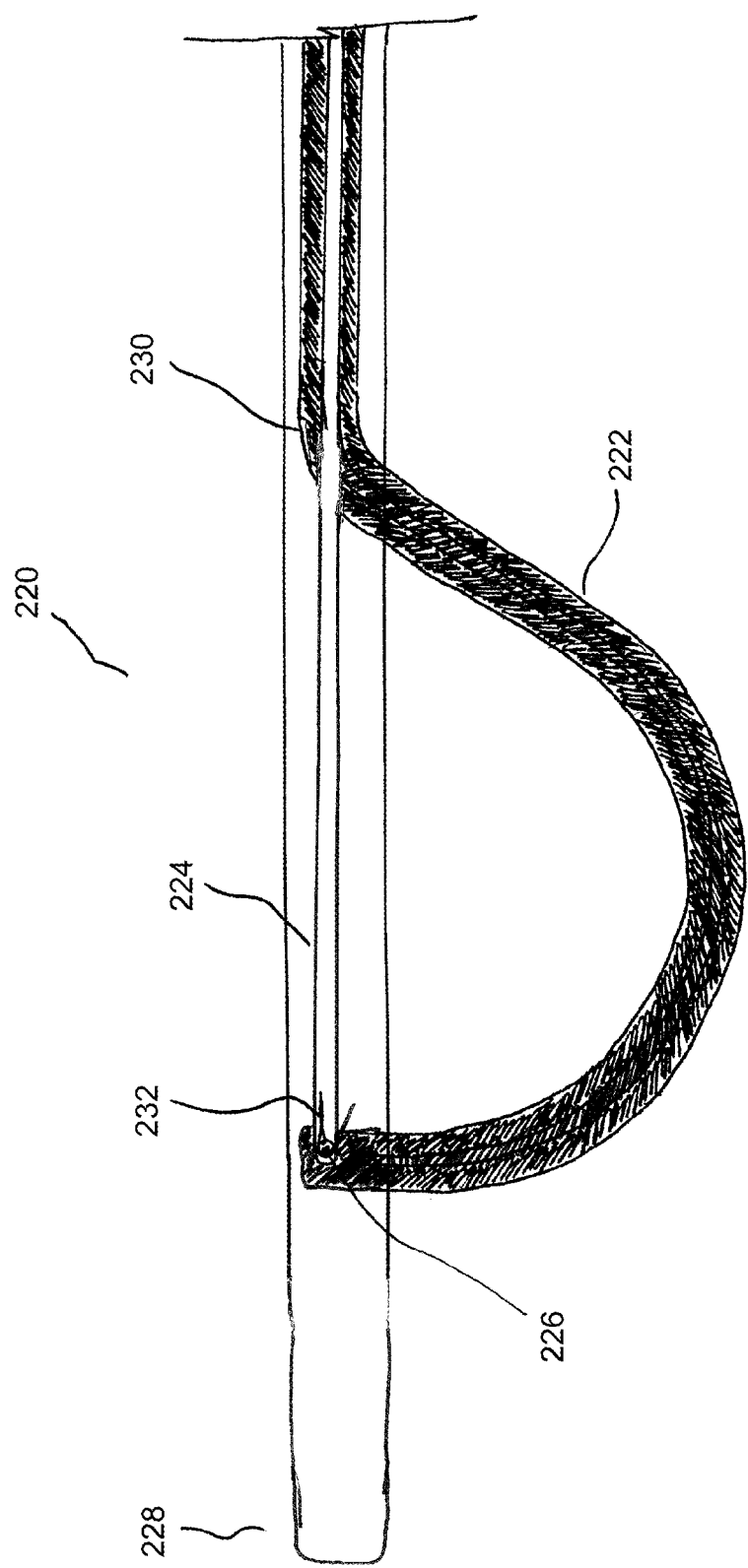
FIG. 17B is another alternative embodiment of an endoscope system in a side-viewing configuration.

FIGS. 17A and 17B show a distal portion 228 of an endoscope system 220 having an accessory channel 222. FIG. 17A shows the accessory channel 222 in a forward-viewing configuration and FIG. 17B shows the accessory channel 222 in a side-viewing configuration. A rail 224 may extend along the length of the distal portion 228 of the endoscope and the accessory channel 222. The rail 224, which may extend to a point outside the body, may be connected to the accessory channel 222 near the distal end of the system 220 via a pin 226. The accessory channel 222 may also be connected to the distal portion 228 of the endoscope system 220 at a point 230 proximal the pin 226 via a pin or other connecting structure or bond. To move the accessory channel 222 from the forward-viewing configuration to the side-viewing configuration, the rail 224 may be moved in a proximal direction, thereby pulling the distal end of the accessory channel 222 proximally via the pin connection 226. Since the accessory channel 222 is also secured to the distal portion 228 at the point 230, the portion of the accessory channel 222 distal the point 230 may bend away from the distal portion 228 as the rail 224 is pulled further in a proximal direction. While this proximal sliding movement is occurring, the accessory channel 222 may also rotate around the connection pin 226, thereby moving the accessory channel 222 to the side-viewing configuration shown in FIG. 17B. The accessory channel 222 may be moved back to the forward-viewing configuration by moving the rail 224 in a distal direction. Alternatively or in combination, the accessory channel 222 may be biased towards the forward-viewing configuration via a spring 232 or other biasing force such that when the proximally directed force on the rail 224 is released, the accessory channel 222 automatically reverts back to the forward-viewing configuration. The rail 224 may preferably be made of a rigid or semi-rigid biocompatible material. While the point 230 at which the accessory channel 222 is secured to the endoscope system 220 is shown near the distal end of the system, the point 230 may be located anywhere along the entire length of the system 220. If multiple accessory channels are used, multiple rails may be used to individually control the accessory channels or a single rail may be used to control both accessory channels simultaneously.

In an alternative design using similar concepts as the endoscope system 220 shown in FIGS. 17A and 17B, the rail 224 may instead be connected to the accessory channel 222 at the point 230 and the accessory channel 222 may be connected to the distal portion 228 of the system 220 at the pin 226. Thus, moving the rail 224 in a distal direction may cause the accessory channel 222 to bend away from the distal portion 228 while rotating around the pin 226, thereby moving the accessory channel 222 to the side-viewing configuration. Further, movement of the rail 224 may thereby move the accessory channel 222 back to the forward viewing configuration. As with the previously described embodiment, the accessory channel 222 may be biased towards the forward-viewing configuration via a spring or other biasing force such that when the distally directed force on the rail 224 is released, the accessory channel 222 automatically reverts back to the forward-viewing configuration.

Figure 18A:
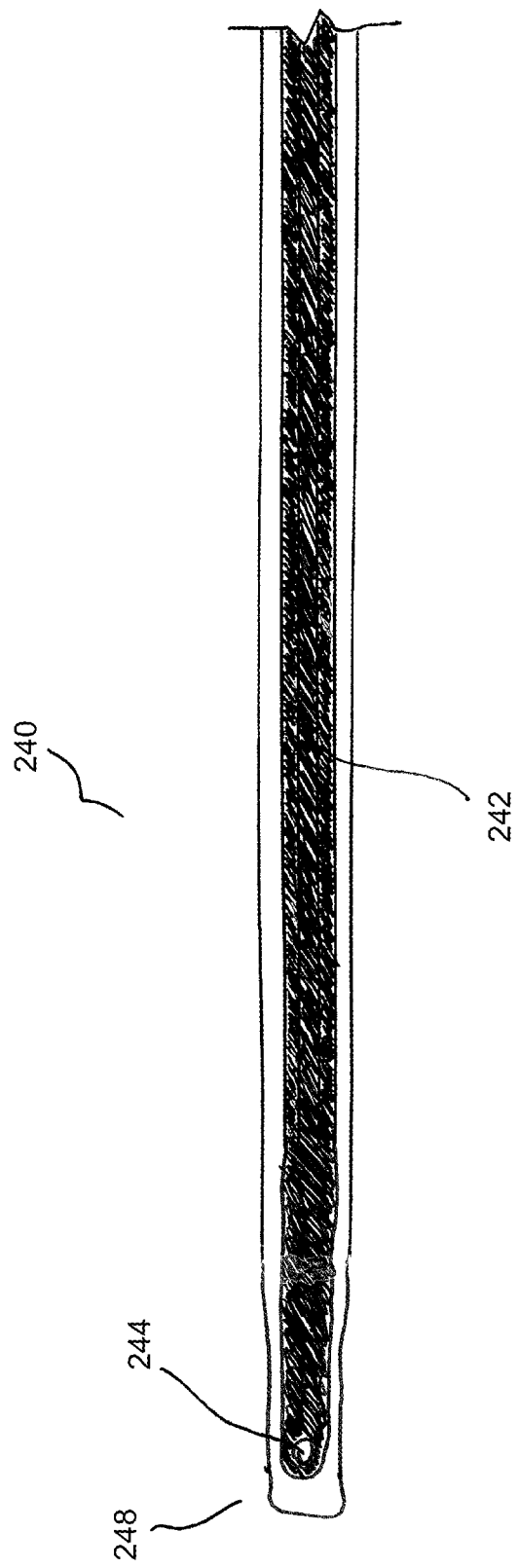
FIG. 18A is yet another alternative embodiment of an endoscope system in a forward-viewing configuration.
Figure 18B:
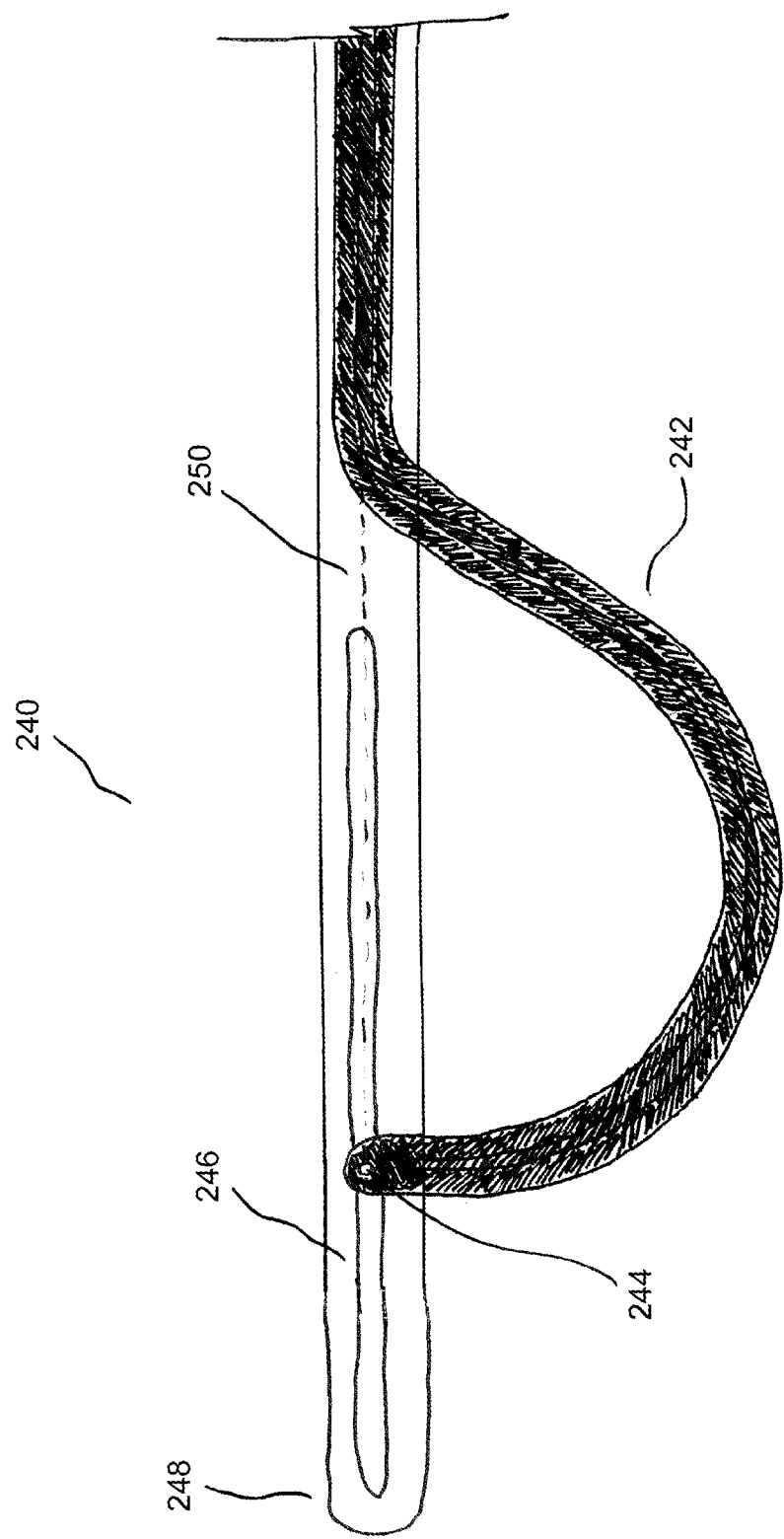
FIG. 18B is yet another alternative embodiment of an endoscope system in a side-viewing configuration.

FIGS. 18A and 18B show a distal portion 248 of an endoscope system 240 having an accessory channel 242. FIG. 18A shows the accessory channel 242 in a forward-viewing configuration and FIG. 18B shows the accessory channel 242 in a side-viewing configuration. In this embodiment, a pin 244 is connected to a distal end of the accessory channel 242. This pin 244 is slidably disposed within a slot 246 formed in the distal portion 248 of the endoscope system 240 (shown in FIG. 18B). A pull member 250 or other elongated member may be attached to the pin 244 or the distal end of the accessory channel 242 and extend along the length of the endoscope system 240 to a point external the patient. To move the accessory channel 242 from the forward-viewing configuration to the side-viewing configuration, the pull member 250 may be pulled in a proximal direction, thereby causing the pin 244 to slide proximally along the slot 246, which in turn pulls the accessory channel 242 proximally. As the accessory channel 242 is pulled proximally, a distal section of the accessory channel 242 bends away from the distal portion 248 of the endoscope system 240 while the accessory channel 242 also rotates about the pin 244, thereby moving the accessory channel 242 to the side-viewing configuration (FIG. 18B). The accessory channel 242 may be biased towards the forward-viewing configuration by a spring or other biasing force. Thus, to move the accessory channel 242 back to the forward-viewing configuration, the proximally directed force on the pull member 250 merely needs to be released to allow the natural biasing force of the accessory channel 242 to automatically revert the accessory channel 242 back to the forward-viewing configuration. If multiple accessory channels are used, multiple pins and slots may be used to individually control the accessory channels or a single pin and/or slot may be used to control both accessory channels simultaneously.

In an alternative design using similar concepts to the endoscope system 240 described above and shown in FIGS. 18A and 18B, the distal end of the accessory channel 242 may instead be rotatably but not slidably connected to the distal portion 248 of the endoscope system 230, while a pin may be attached to the accessory channel 242 at a point proximal the distal end of the accessory channel 242. This pin may be slidably received in a slot, thereby allowing the accessory channel 242 to slide back and forth between forward and side-viewing configurations while the distal end of the accessory channel 242 remains slidably fixed in place. In one example, the accessory channel 242 may be biased towards the side-viewing configuration by a spring or other biasing force. Thus, to move the accessory channel 242 to the forward-viewing configuration, a proximally directed force may be applied to the pull member 250 which then pulls the accessory channel 242 proximally and to the forward-viewing configuration. To then move the accessory channel 242 back to the side-viewing configuration, the proximally applied force to the pull member 250 merely needs to be released to allow the natural biasing force of the accessory channel 242 to automatically revert the accessory channel 242 back to the side-viewing configuration.

Figure 19A:
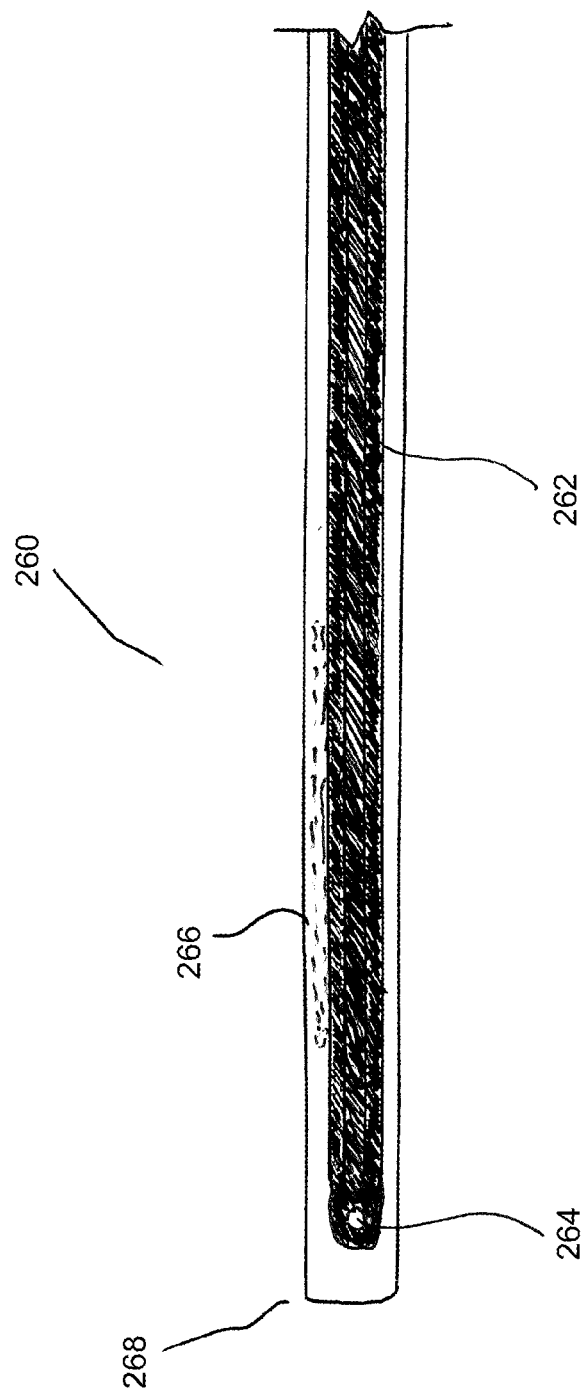
FIG. 19A is yet another alternative embodiment of an endoscope system in a forward-viewing configuration.
Figure 19B:
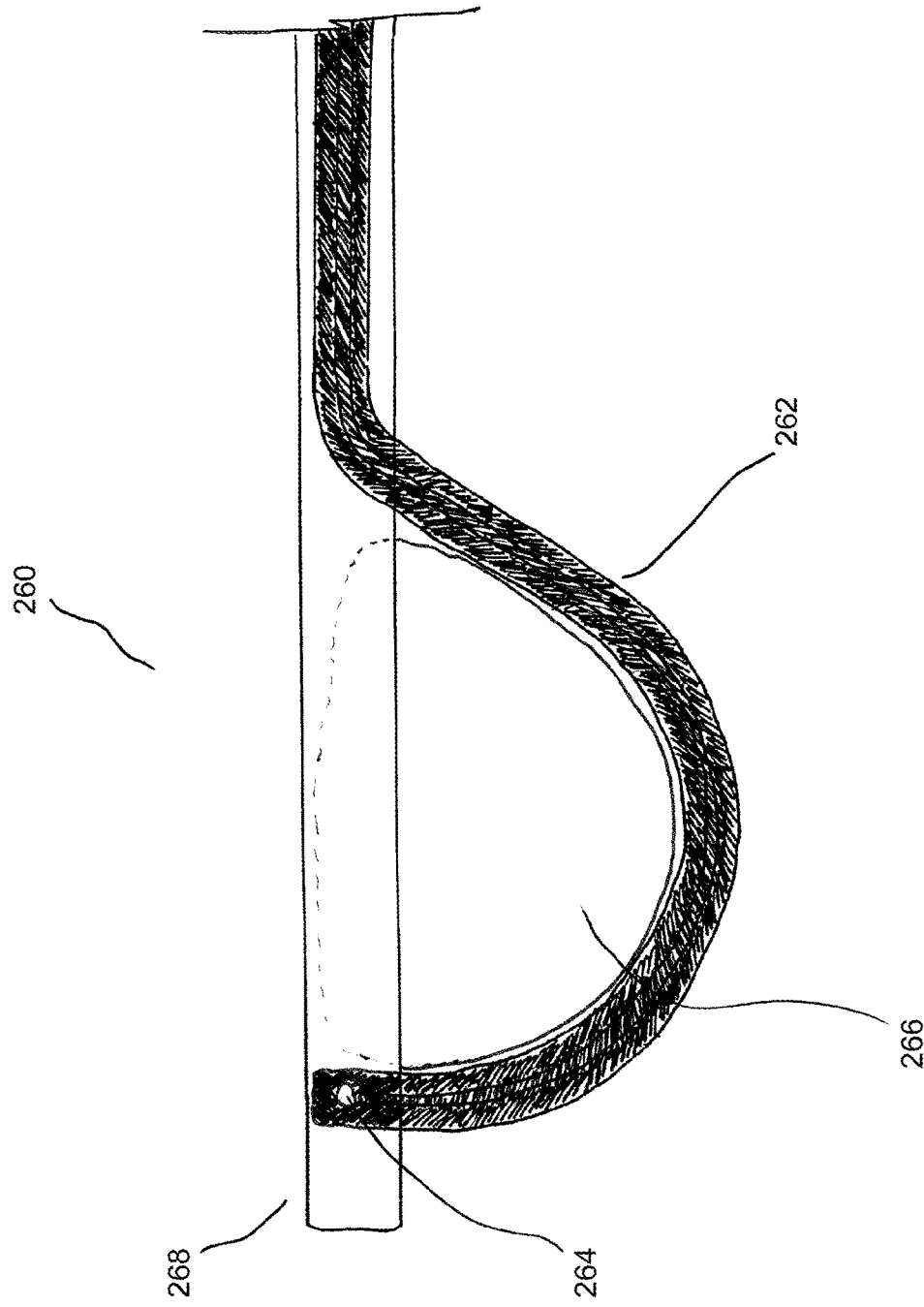
FIG. 19B is yet another alternative embodiment of an endoscope system in a side-viewing configuration.

FIGS. 19A and 19B show a distal portion 268 of an endoscope system 260 having an accessory channel 262. FIG. 19A shows the accessory channel 262 in a forward-viewing configuration and FIG. 19B shows the accessory channel 262 in a side-viewing configuration. The distal end of the accessory channel 262 may be pivotably attached to the distal portion 268 of the endoscope system 260 via a pin 264. An inflatable balloon 266 may be connected to the distal portion 268 of the scope system 260 and disposed adjacent to the accessory channel 262 and proximal the pin 264. To move the accessory channel 262 from the forward-viewing configuration to the side-viewing configuration, the balloon 266 may be inflated, which thereby contacts and pushes a section of the accessory channel 262 away from the distal portion 268 as the accessory channel 262 also rotates around the pin 264. To move the accessory channel 262 back to the forward-viewing configuration, the balloon 266 may be deflated. The accessory channel 262 may be biased towards the forward-viewing configuration via a spring or other biasing force such that when the balloon 266 is deflated, the accessory channel 262 automatically reverts back to the forward-viewing configuration. The balloon 266 may be inflated and deflated in a variety of ways and with a variety of fluids, including with the use of an inflation lumen that extends from the balloon 266 to a point external the patient. The balloon 266 may also just contact or fully connect to the accessory channel 262. For example, an adhesive or sleeve may be used to connect the balloon 266 and accessory channel 262. Further, the balloon 266 itself can have a variety of shapes, including a groove within which the accessory channel 262 can rest. In an alternative embodiment, the balloon 266 may be attached to the accessory channel 262 and not the distal portion 268 of the scope system 260. Instead, when the balloon 266 is inflated the balloon 266 may just contact the distal portion 268 and push the accessory channel 262 away from the distal portion 268.

Figure 20A:
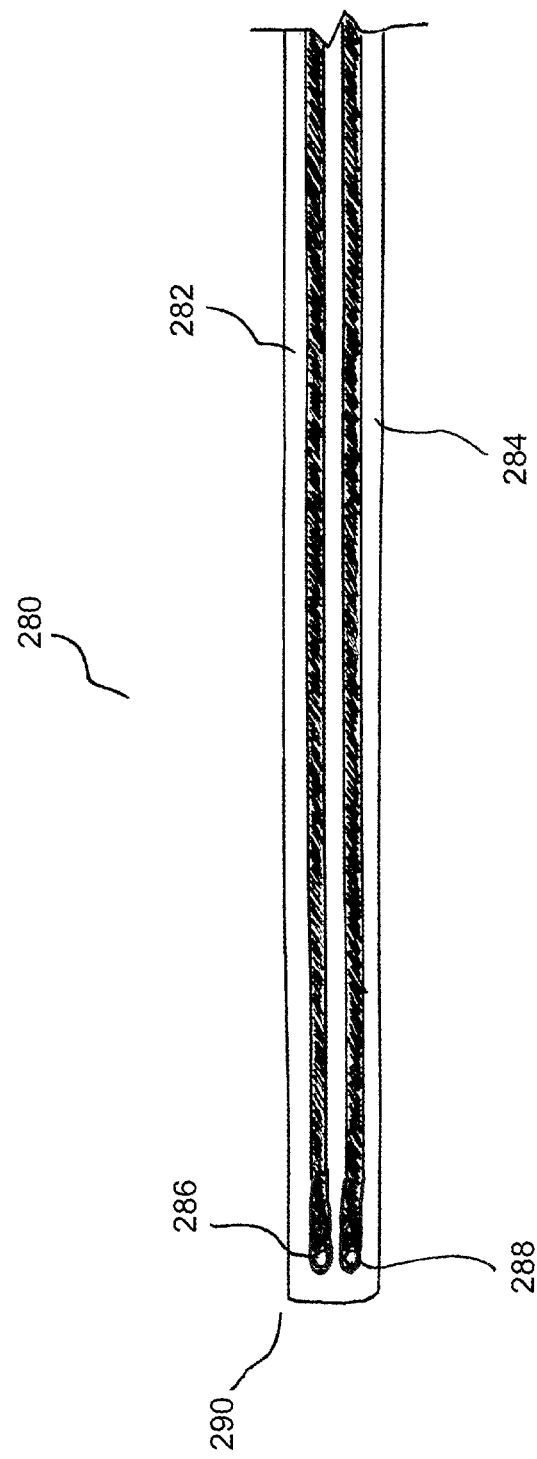
FIG. 20A is yet another alternative embodiment of an endoscope system in a forward-viewing configuration.
Figure 20B:
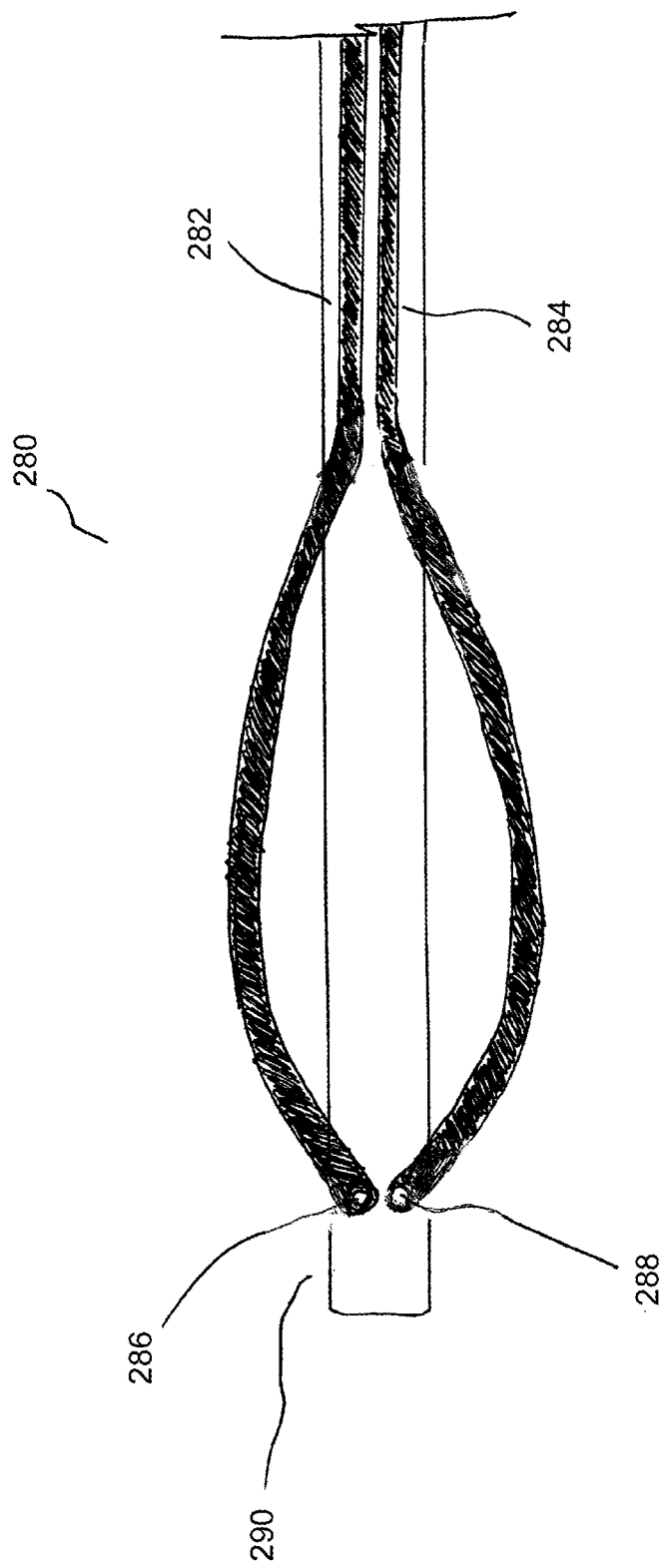
FIG. 20B is yet another alternative embodiment of an endoscope system in a side-viewing configuration.

FIGS. 20A and 20B show a distal portion 290 of an endoscope system 280 having a first accessory channel 282 and a second accessory channel 284. FIG. 20A shows the accessory channels 282, 284 in a forward-viewing configuration and FIG. 20B shows the accessory channels 282, 284 in a side-viewing configuration. The distal end of the first accessory channel 282 may be secured to the distal portion 290 of the endoscope system 280 via a pin 286 while the distal end of the second accessory channel 284 may be secured to the distal portion 290 of the endoscope system 280 via a pin 288. These accessory channels 282, 284 may be individually pivotable between forward-viewing and side-viewing configurations. Further, the accessory channels 282, 284 may pivot in different planes, as shown in FIG. 20B, thereby allowing various directions of access to a target site. The accessory channels 282, 284 may be advanced distally and retracted proximally to move the accessory channels 282, 284 between the forward and side-viewing configurations. However, various other designs may be used to move the accessory channels 282, 284, including the designs discussed in the previous and subsequent embodiments. Further, all other embodiments discussed herein may include multiple accessory channels that are designed to move independently of one another and/or in different planes, as desired.

Figure 21A:
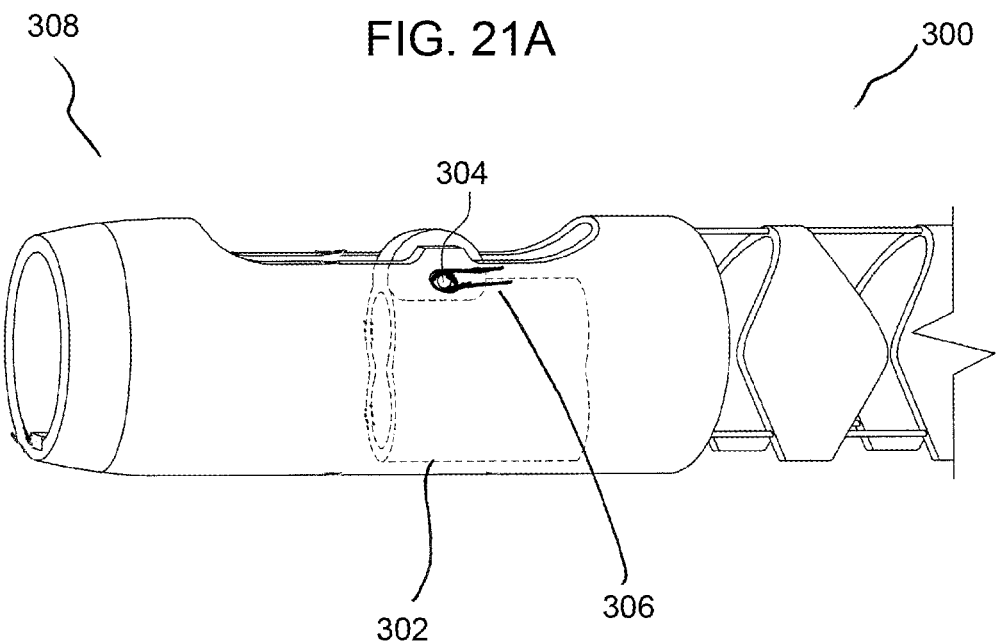
FIG. 21A is yet another alternative embodiment of an endoscope system in a forward-viewing configuration.
Figure 21B:
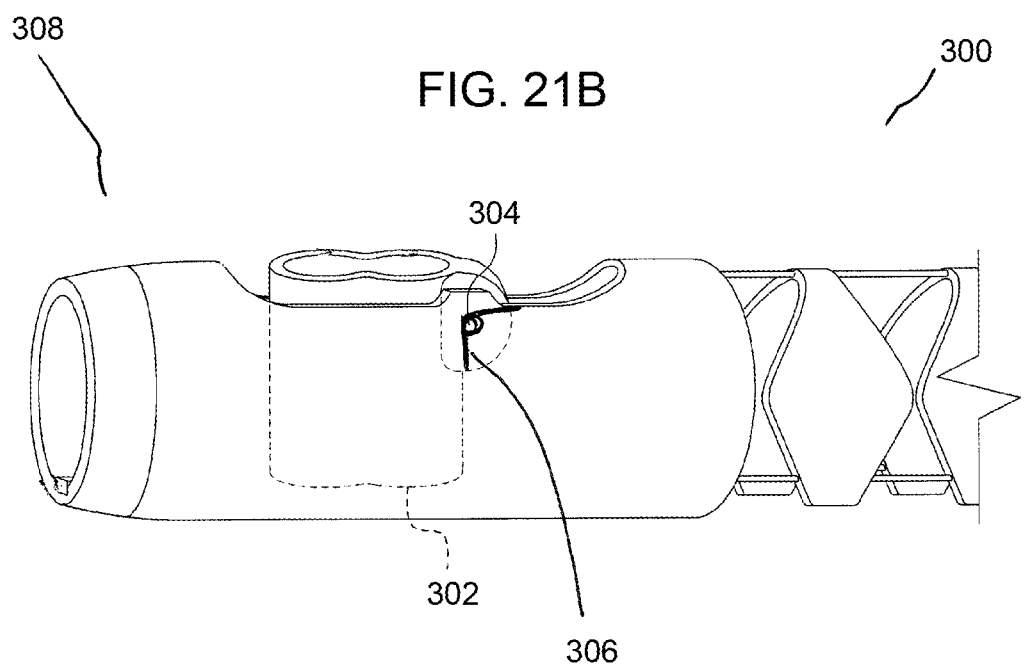
FIG. 21B is yet another alternative embodiment of an endoscope system in a side-viewing configuration.

FIGS. 21A and 21B show a distal portion 308 of an endoscope system 300 having a pivot arm 302 that is rotatable around a pivot point 304. As with previously described embodiments, accessory channels (not shown), may be disposed within or adjacent to the pivot arm 302, such that rotation of the pivot arm 302 from the position in FIG. 21A to the position in FIG. 21B causes movement of the accessory channels from the forward-viewing configuration to the side-viewing configuration. In this embodiment, a torsion spring 306 is disposed around the pivot point 304. The torsion spring 306 biases the pivot arm 302 towards the side-viewing configuration. Thus, when no external force is applied to the accessory channels or pivot arm 302, the accessory channels and pivot arm 302 naturally move to, or stay in, the side-viewing configuration. To move the accessory channels and pivot arm 302 to the forward-viewing configuration, the accessory channels or pivot arm 302 may be pulled or moved in a proximal direction, thereby moving against the biasing force of the torsion spring 306. To move the accessory channels and pivot arm 302 back to the side-viewing configuration, the proximally directed force previously applied to the accessory channels and pivot arm 302 may be released and the accessory channels and pivot arm 302 will naturally revert back to the side-viewing configuration due to the biasing force of the torsion spring 306. While this embodiment utilizes a torsion spring 306, any other spring or biasing member may be used to bias the pivot arm 304. Alternatively, the pivot arm 302 may be biased towards the forward-viewing configuration. Further, the torsion spring 306 or other biasing member may directly bias the accessory channels without the use of the pivot arm 304.

Figure 22A:
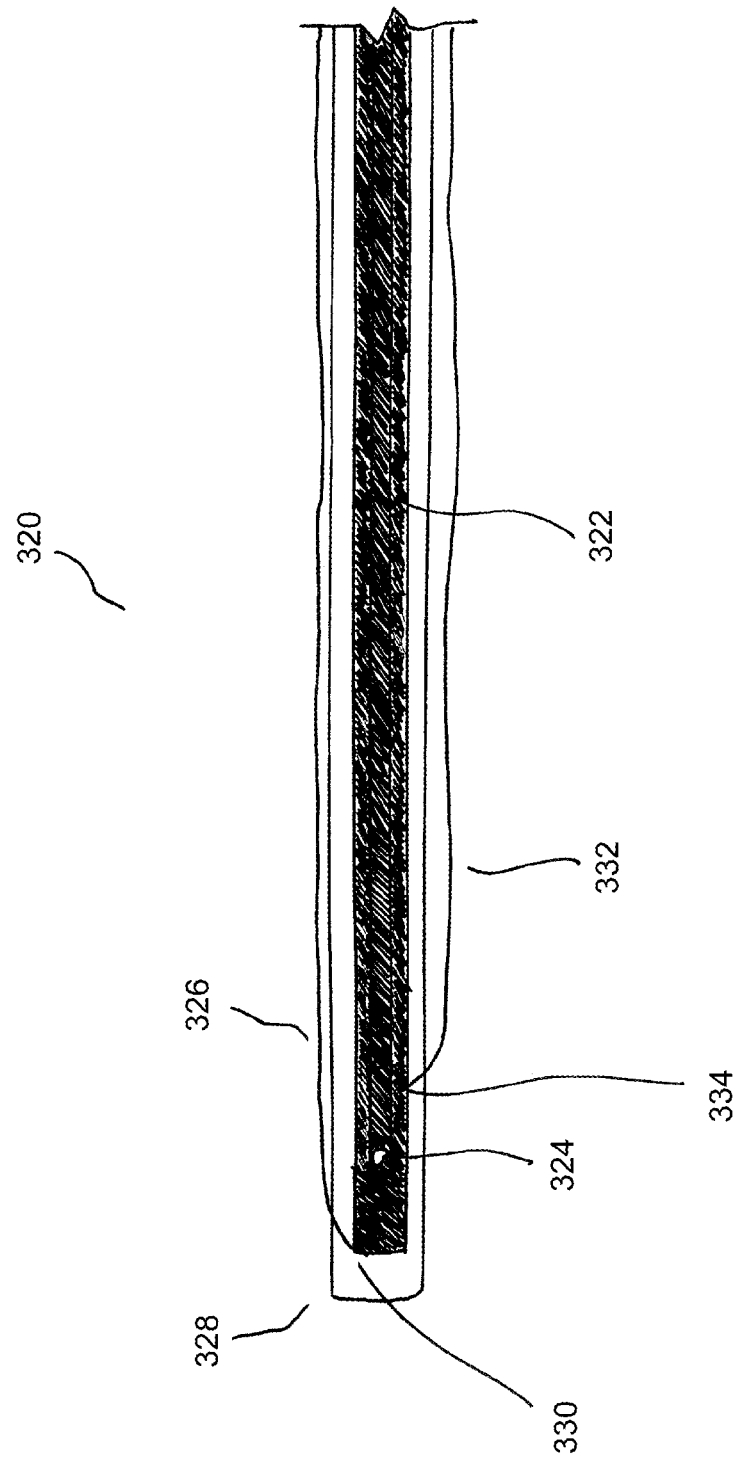
FIG. 22A is yet another alternative embodiment of an endoscope system in a forward-viewing configuration.
Figure 22B:
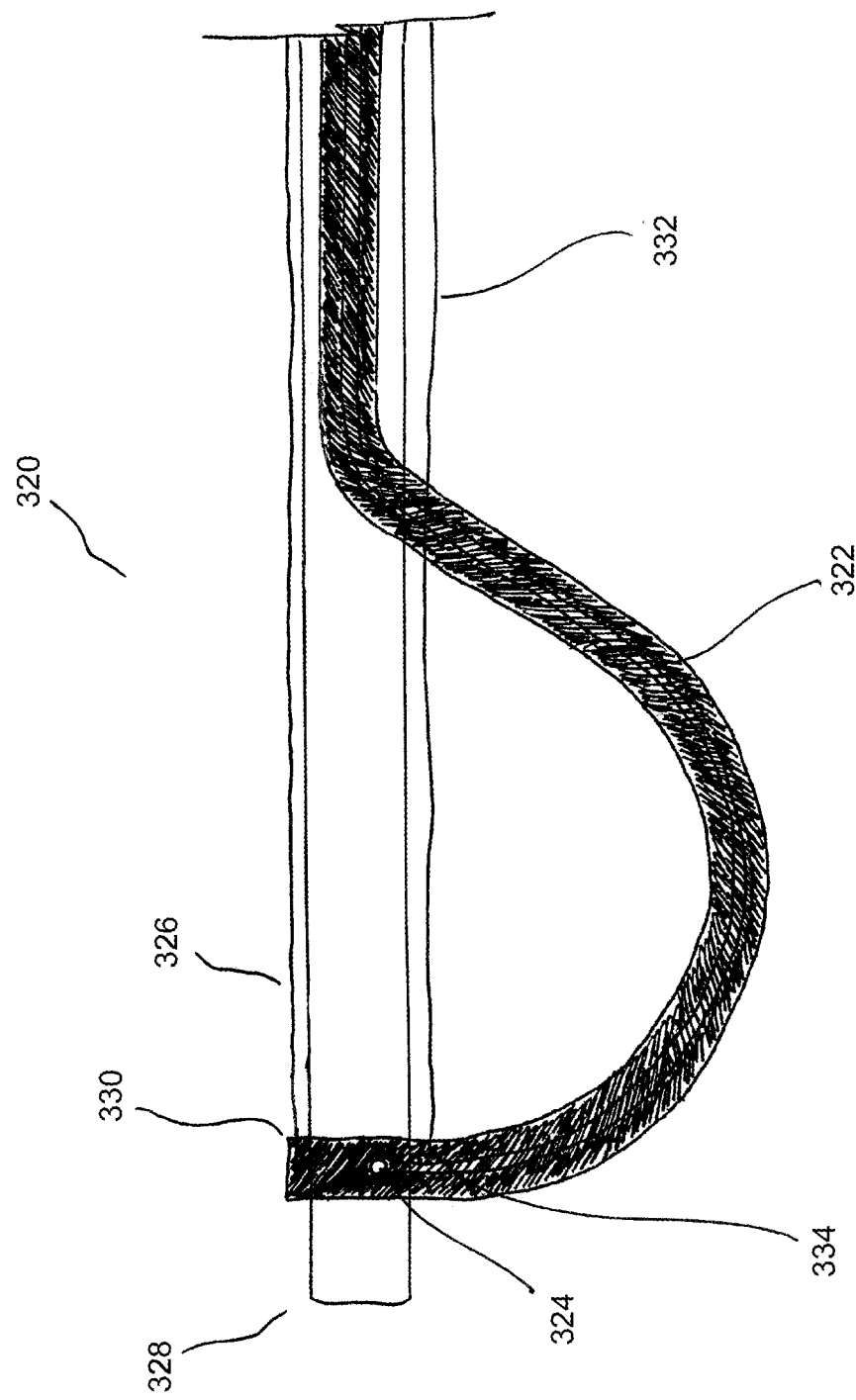
FIG. 22B is yet another alternative embodiment of an endoscope system in a side-viewing configuration.

FIGS. 22A and 22B show a distal portion 328 of an endoscope system 320 having an accessory channel 322. FIG. 22A shows the accessory channel 322 in a forward-viewing configuration and FIG. 22B shows the accessory channel 322 in a side-viewing configuration. The accessory channel 322 may be secured to the distal portion 328 via a pin 324. A pull member 326 may be connected to the accessory channel 322 at a point 330 distal the pin 324. The pull member 326 may extend from the point 330 distal the pin 324 along the length of the endoscope system 320 to a point external the patient. To move the accessory channel 322 to the side-viewing configuration, a proximally directed force may be applied to the pull member 326 which moves the pull member 326 and the portion of the accessory channel 322 that is distal the pin 324 in a proximal direction. As this proximal movement happens, the accessory channel 322 also rotates about the pin 324, thereby causing a section of the accessory channel to bend away from the distal portion 328 and to the side-viewing configuration shown in FIG. 22B. To move the accessory channel 322 back to the forward-viewing configuration, the proximally directed force that was applied to the pull member 326 may be released. The accessory channel 322 may be biased towards the forward-viewing configuration via a spring or other biasing force such that when the force on the pull member 326 is released, the accessory channel 322 automatically reverts back to the forward-viewing configuration. Alternatively or in addition, a second pull member 332 may be attached to the accessory channel 322 at a point 334 proximal the pin 324 and extend proximally along the endoscope system 320 to a point external the patient. Thus, to move the accessory channel 322 back to the forward-viewing configuration, a proximally directed force may be applied to this second pull member 332. Further, the accessory channel 322 may be biased towards the side-viewing configuration instead of towards the forward-viewing configuration. Thus, this second pull member 332 that is attached to the accessory channel 322 at a point 334 proximal the pin 324 may be used without the first pull member 326 to move the accessory channel 322 between the forward and side-viewing configurations. The pull members 326, 332 may extend along the length of the endoscope system 320 either inside or outside of the lumen of the system 320, or through dedicated pull member lumens. It may be beneficial to use the handle 13 shown in FIG. 10 or a similar handle with this embodiment. For example, one of the pull members 326 or 332 may be attached to the arm 44 while the remaining pull member 326 or 332 may be attached to the first slider 46. Thus, the arm 44 and first slider 46 may be manipulated to pull the pull members 326, 332, thereby moving the accessory channel 322 between the forward-viewing and side-viewing configurations. Alternatively, a rotatable wheel or cam may be coupled to the handle 13 and attached to the pull members 326, 332. Or a single pull member may be used in lieu of the pull members 326, 332 that extends from the distal portion 328 of the scope system 320, to the handle 13, around a wheel, cam, or other mechanical control member, and then back towards the distal portion 328.

The various embodiments described above are not separate and distinct. They are interchangeable, and features from different embodiments may be combined as desired. Further, a scope system may utilize components of one embodiment to move one accessory channel between forward-viewing and side-viewing configurations while the scope system utilizes components of another embodiment to move another accessory channel between forward-viewing and side-viewing configurations. For example, a scope system with two accessory channels may have a first accessory channel that is operated with a pin and slot as described in FIGS. 18A and 18B while the second accessory channel is operated with a linkage as described in FIGS. 16A and 16B.

While the embodiments described herein are shown in reference to the endoscopy field and endoscopic retrograde cholangiopancreatography procedures, the embodiments may be used in a variety of other medical procedures including endoscopic submucosal dissection and any other endoscopic procedure that would benefit by having multiple instruments at a time and/or the ability to see things from both the forward-viewing and side-viewing perspectives.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A scope system, comprising:
an elongate tube comprising a lumen extending therethrough, the elongate tube further comprising a distal portion terminating in a distal-most end;
at least one accessory channel extending from a proximal end to a distal end and comprising an accessory lumen extending therethrough, the at least one accessory channel movably disposed at least partially within the lumen of the elongate tube, the at least one accessory channel comprising a distal section terminating in a distal viewing end, the at least one accessory channel further comprising a forward-viewing configuration and a side-viewing configuration; and
a camera system disposed within the distal section of the accessory channel;
wherein the distal viewing end of the at least one accessory channel is rotatably coupled to the distal end portion of the elongate tube;
the distal portion defining a side opening having a length and providing access from the lumen to a point external the elongate tube, the side opening being spaced proximally of the distal-most end of the distal portion, the distal portion comprising a pin defining a pivot point about which the at least one accessory channel is configured to rotate, the pin being disposed within the length of the side opening in a longitudinal dimension;
wherein the distal viewing end of the at least one accessory channel is disposed within the distal portion of the elongate tube in both the forward-viewing configuration and the side-viewing configuration;
wherein, when in the forward-viewing configuration, a distal-most end of the distal viewing end of the at least one accessory channel is aligned with a longitudinal direction of the distal portion of the elongate tube;
wherein, when in the side-viewing configuration, the distal viewing end of the at least one accessory channel is disposed at an angle relative to the distal portion of the elongate tube; and
wherein, when in the side-viewing configuration, a portion of the distal section of the at least one accessory channel is disposed outside the lumen of the elongate tube.

2. The scope system of claim 1, wherein:
movement of a proximal portion of the at least one accessory channel in a distal direction relative to the elongate tube moves the at least one accessory channel from the forward-viewing configuration to the side-viewing configuration.

3. The scope system of claim 2, wherein:
movement of the proximal portion of the at least one accessory channel in a proximal direction relative to the elongate tube moves the at least one accessory channel from the side-viewing configuration to the forward-viewing configuration.

4. The scope system of claim 1, wherein:
during movement of the at least one accessory channel between the forward-viewing configuration and the side-viewing configuration, the at least one accessory channel rotates about the pivot point.

5. The scope system of claim 4, wherein:
the at least one accessory channel is biased towards the side-viewing configuration.

6. The scope system of claim 4, wherein:
a pull member attached to the at least one accessory channel at a point distal the pivot point, wherein the pull member extends proximally from the point;
wherein movement of the pull member in a proximal direction moves the at least one accessory channel from the forward-viewing configuration to the side-viewing configuration.

7. The scope system of claim 6, wherein:
the pull member is a first pull member and the point is a first point;
the scope system further comprises a second pull member attached to the at least one accessory channel at a second point proximal the pivot point, wherein the second pull member extends proximally from the second point;
wherein movement of the second pull member in a proximal direction moves the at least one accessory channel from the side-viewing configuration to the forward-viewing configuration.

8. The scope system of claim 1, wherein:
the at least one accessory channel is biased towards the forward-viewing configuration.

9. The scope of claim 1, wherein:
a spring disposed around the pivot point, the spring biasing the at least one accessory channel towards the forward-viewing configuration.

10. The scope system of claim 1, wherein:
the at least one accessory channel comprises a first accessory channel and a second accessory channel, wherein the first accessory channel is movable between the forward-viewing configuration and the side-viewing configuration independent from the second accessory channel.

11. The scope system of claim 10, wherein:
the first accessory channel moves between the forward-viewing configuration and side-viewing configuration in a different plane from where the second accessory channel moves between the forward-viewing configuration and the side-viewing configuration.

12. The scope system of claim 10, further comprising:
a proximal link and a distal link, wherein the proximal link comprises a first end pivotally attached to the at least one accessory channel and a second end pivotally attached to the at least one accessory channel distal the first end of the proximal link, wherein the distal link comprises a first end pivotally attached to the second end of the proximal link and a second end pivotally attached to the at least one accessory channel distal the second end of the proximal link, wherein the second end of the distal link is also pivotally attached to the distal portion of the elongate tube;
wherein during movement of the at least one accessory channel from the forward-viewing configuration to the side-viewing configuration, the second end of the proximal link and first end of the distal link move with the at least one accessory channel radially away from the distal end portion of the elongate tube.

13. The scope system of claim 1, further comprising:
a rail extending from a proximal end to a distal end, wherein the rail is pivotally attached to the at least one accessory channel at a first point;
wherein the at least one accessory channel is longitudinally fixed with respect to the elongate tube at a second point proximal the first point;
wherein movement of the rail in a proximal direction moves the at least one accessory channel from the forward-viewing configuration to the side-viewing configuration.

14. The scope system of claim 13, wherein:
movement of the rail in a distal direction moves the at least one accessory channel from the side-viewing configuration to the forward-viewing configuration.

15. The scope system of claim 1, further comprising:
a rail extending from a proximal end to a distal end, wherein the rail is pivotally attached to the at least one accessory channel at a first point;
wherein the at least one accessory channel is longitudinally fixed with respect to the elongate tube at a second point distal the first point;
wherein movement of the rail in a distal direction moves the at least one accessory channel from the forward-viewing configuration to the side-viewing configuration.

16. The scope system of claim 1, wherein:
the distal end portion of the elongate tube further comprises a slot extending longitudinally along the distal end portion;
the at least one accessory channel is connected to the distal end portion of the elongate tube via a pin slidably disposed within the slot, wherein a pull member extends proximally from the pin; and
application of a proximally directed force to the pull member slides the pin proximally along the slot and moves the at least one accessory channel from the forward-viewing configuration to the side-viewing configuration.

17. The scope system of claim 16, wherein:
the at least one accessory channel is biased towards the forward-viewing configuration, wherein the at least one accessory channel is configured to automatically move from the side-viewing configuration to the forward-viewing configuration upon release of the proximally directed force applied to the pull member.

18. The scope system of claim 1, wherein:
the distal end portion of the elongate tube further comprises a slot extending longitudinally along the distal portion;
the at least one accessory channel is connected to the distal end portion of the elongate tube via a first pin slidably disposed within the slot, wherein a pull member extends proximally from the first pin, wherein the at least one accessory channel is further rotatably connected to the distal end portion of the elongate tube via a second pin located distal the first pin; and
application of a proximally directed force to the pull member slides the first pin proximally along the slot and moves the at least one accessory channel from the side-viewing configuration to the forward-viewing configuration.

19. The scope system of claim 18, wherein:
the at least one accessory channel is biased towards the side-viewing configuration, wherein the at least one accessory channel is configured to automatically move from the forward-viewing configuration to the side-viewing configuration upon release of the proximally directed force applied to the pull member.

20. The scope system of claim 1, further comprising:
an inflatable balloon contacting the distal section of the at least one accessory channel, wherein the at least one accessory channel is pivotally connected to the distal end portion of the elongate tube at a point distal the inflatable balloon;
wherein inflation of the inflatable balloon moves the at least one accessory channel from the forward-viewing configuration to the side-viewing configuration.

21. The scope system of claim 1, wherein:
when in the side-viewing configuration, the portion of the distal section of the at least one accessory channel is arced away from the lumen of the elongate tube.

* * * * *